(12) United States Patent
Choy et al.

(10) Patent No.: US 12,233,415 B2
(45) Date of Patent: Feb. 25, 2025

(54) MICROFLUIDIC REACTION CHAMBER FOR AMPLIFICATION OF NUCLEIC ACIDS

(71) Applicant: Hewlett-Packard Development Company, L.P., Spring, TX (US)

(72) Inventors: Si-lam Choy, Corvallis, OR (US); Hilary Ely, Corvallis, OR (US); John Lahmann, Corvallis, OR (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 642 days.

(21) Appl. No.: 17/417,306

(22) PCT Filed: Apr. 29, 2019

(86) PCT No.: PCT/US2019/029707
§ 371 (c)(1),
(2) Date: Jun. 22, 2021

(87) PCT Pub. No.: WO2020/222763
PCT Pub. Date: Nov. 5, 2020

(65) Prior Publication Data
US 2022/0048026 A1 Feb. 17, 2022

(51) Int. Cl.
*B01L 3/00* (2006.01)
*A61L 27/16* (2006.01)
(Continued)

(52) U.S. Cl.
CPC ..... *B01L 3/50273* (2013.01); *B01L 3/502761* (2013.01); *B01L 7/52* (2013.01);
(Continued)

(58) Field of Classification Search
CPC .. B01L 3/50273; B01L 3/502761; B01L 7/52; B01L 2200/0621; B01L 2200/10;
(Continued)

(56) References Cited

U.S. PATENT DOCUMENTS 7,892,819 B2   2/2011  Wilding et al.
8,623,789 B2   1/2014  Belgrader et al.
(Continued)

FOREIGN PATENT DOCUMENTS

EP    2026074        2/2009
EP    3329995 A2     6/2018
(Continued)

*Primary Examiner* — Jennifer Wecker
*Assistant Examiner* — Oyeleye Alexander Alabi
(74) *Attorney, Agent, or Firm* — Foley & Lardner LLP

(57) ABSTRACT

Examples herein involve amplification and detection of nucleic acids using a microfluidic reaction chamber. An example apparatus includes a reaction-chamber circuit to process a reagent and a biologic sample for amplification of nucleic acids. The apparatus further includes a plurality of capillaries to pass the reagent and the biologic sample through the microfluidic reaction chamber. A valve control system may selectively control each of a plurality of valves to cause the reagent and the biologic sample to selectively move through the microfluidic reaction chamber for the amplification of the nucleic acids according to a particular timing sequence. In various examples, a trapping region disposed in the microfluidic reaction chamber secures the nucleic acids in the microfluidic reaction chamber for amplification using the reaction-chamber circuit.

6 Claims, 20 Drawing Sheets

(51) Int. Cl.

| | |
|---|---|
| A61L 27/56 | (2006.01) |
| B01F 23/00 | (2022.01) |
| B01F 23/41 | (2022.01) |
| B01F 101/23 | (2022.01) |
| B01L 7/00 | (2006.01) |
| B01L 9/00 | (2006.01) |
| B23Q 17/24 | (2006.01) |
| C07K 14/705 | (2006.01) |
| C08F 220/56 | (2006.01) |
| C08L 33/26 | (2006.01) |
| C12M 1/34 | (2006.01) |
| C12Q 1/04 | (2006.01) |
| C12Q 1/18 | (2006.01) |
| C12Q 1/6844 | (2018.01) |
| C12Q 1/686 | (2018.01) |
| G01N 1/31 | (2006.01) |
| G01N 21/17 | (2006.01) |
| G01N 21/3577 | (2014.01) |
| G01N 21/359 | (2014.01) |
| G01N 21/39 | (2006.01) |
| G01N 21/45 | (2006.01) |
| G01N 21/64 | (2006.01) |
| G01N 21/77 | (2006.01) |
| G01N 21/78 | (2006.01) |
| G01N 27/414 | (2006.01) |
| G01N 30/12 | (2006.01) |
| G01N 30/68 | (2006.01) |
| G01N 30/70 | (2006.01) |
| G01N 30/72 | (2006.01) |
| G01N 30/88 | (2006.01) |
| G01N 33/00 | (2006.01) |
| G01N 33/18 | (2006.01) |
| G01N 33/50 | (2006.01) |
| G01N 33/53 | (2006.01) |
| G01N 33/543 | (2006.01) |
| G01N 33/68 | (2006.01) |
| G01N 33/74 | (2006.01) |
| G01N 35/00 | (2006.01) |
| G01N 35/10 | (2006.01) |
| G06T 7/00 | (2017.01) |
| G06T 7/90 | (2017.01) |
| H10K 10/46 | (2023.01) |
| H10K 85/00 | (2023.01) |
| H10K 85/20 | (2023.01) |

(52) U.S. Cl.
CPC .... *C12Q 1/6844* (2013.01); *B01L 2200/0621* (2013.01); *B01L 2200/10* (2013.01); *B01L 2300/0816* (2013.01); *B01L 2300/0867* (2013.01); *B01L 2300/0883* (2013.01); *B01L 2400/0406* (2013.01); *B01L 2400/043* (2013.01); *B01L 2400/0442* (2013.01); *B01L 2400/0633* (2013.01); *B01L 2400/0694* (2013.01)

(58) Field of Classification Search
CPC ..... B01L 2300/0816; B01L 2300/0867; B01L 2300/0883; B01L 2400/0406; B01L 2400/043; B01L 2400/0442; B01L 2400/0633; B01L 2400/0694; B01L 3/502738; B01L 2200/0668; B01L 2400/0478; C12Q 1/6844
See application file for complete search history.

(56) References Cited

U.S. PATENT DOCUMENTS

| | | |
|---|---|---|
| 9,012,236 B2 | 4/2015 | Jovanovich et al. |
| 9,988,668 B2 | 6/2018 | Ding et al. |
| 2004/0086400 A1 | 5/2004 | Blakley |
| 2004/0086427 A1 | 5/2004 | Childers et al. |
| 2004/0086870 A1 | 5/2004 | Tyvoll et al. |
| 2010/0184020 A1 | 7/2010 | Beer |
| 2012/0244604 A1 | 9/2012 | Kornilovich et al. |
| 2013/0331298 A1 | 12/2013 | Rea |
| 2016/0114319 A1 | 4/2016 | McGuinness et al. |
| 2016/0341337 A1 | 11/2016 | Govyadinov et al. |
| 2016/0367981 A1* | 12/2016 | Wunderle ......... B01L 3/502738 |
| 2017/0144155 A1 | 5/2017 | Bohm et al. |
| 2018/0015460 A1 | 1/2018 | Sells et al. |
| 2018/0021776 A1 | 1/2018 | Giri et al. |
| 2018/0214866 A1 | 8/2018 | Torniainen et al. |
| 2018/0229230 A1 | 8/2018 | Chung et al. |
| 2019/0001335 A1 | 1/2019 | Torniainen et al. |

FOREIGN PATENT DOCUMENTS

| | | |
|---|---|---|
| WO | WO-2006121997 | 11/2006 |
| WO | WO-2016205428 A1 | 12/2016 |
| WO | WO-2017119904 | 7/2017 |
| WO | WO-2018151726 | 8/2018 |
| WO | WO-2018186880 | 10/2018 |
| WO | WO-2019013825 | 1/2019 |

* cited by examiner

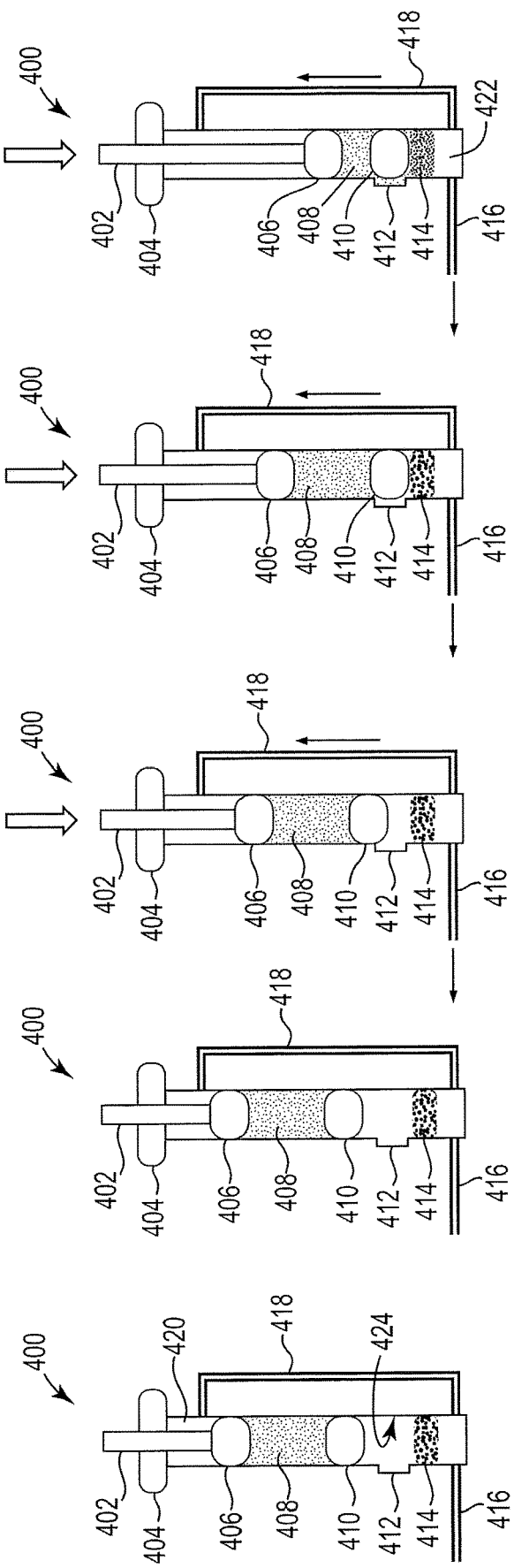

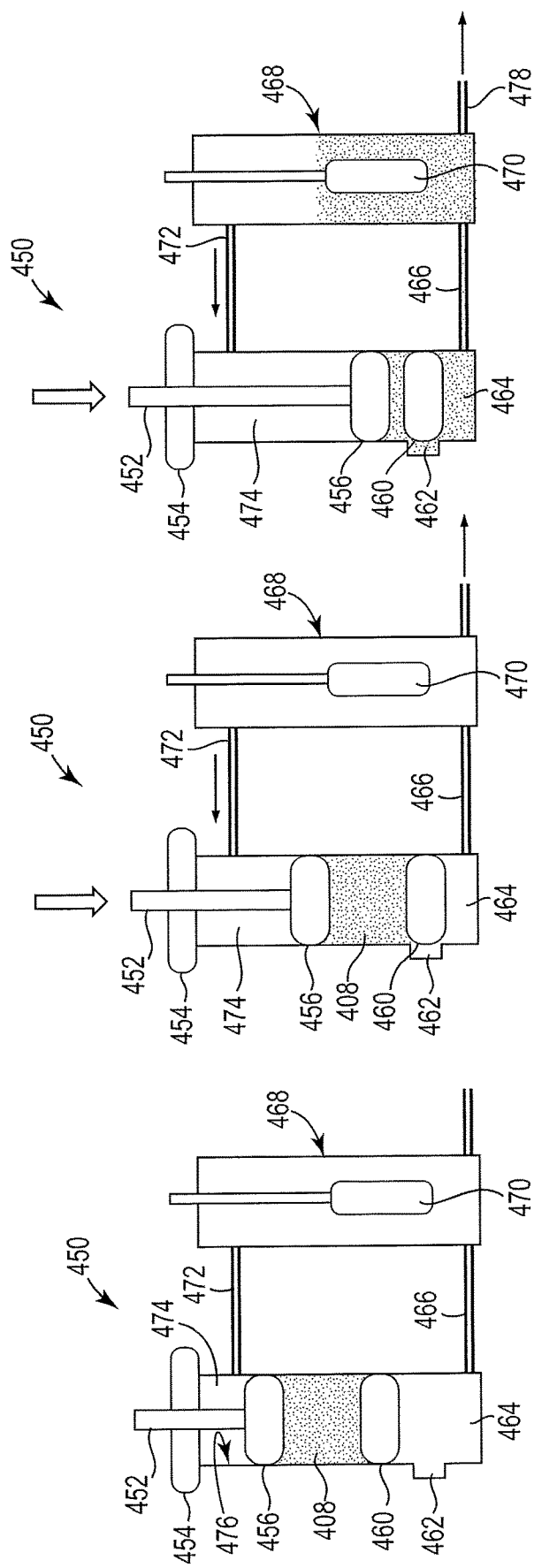

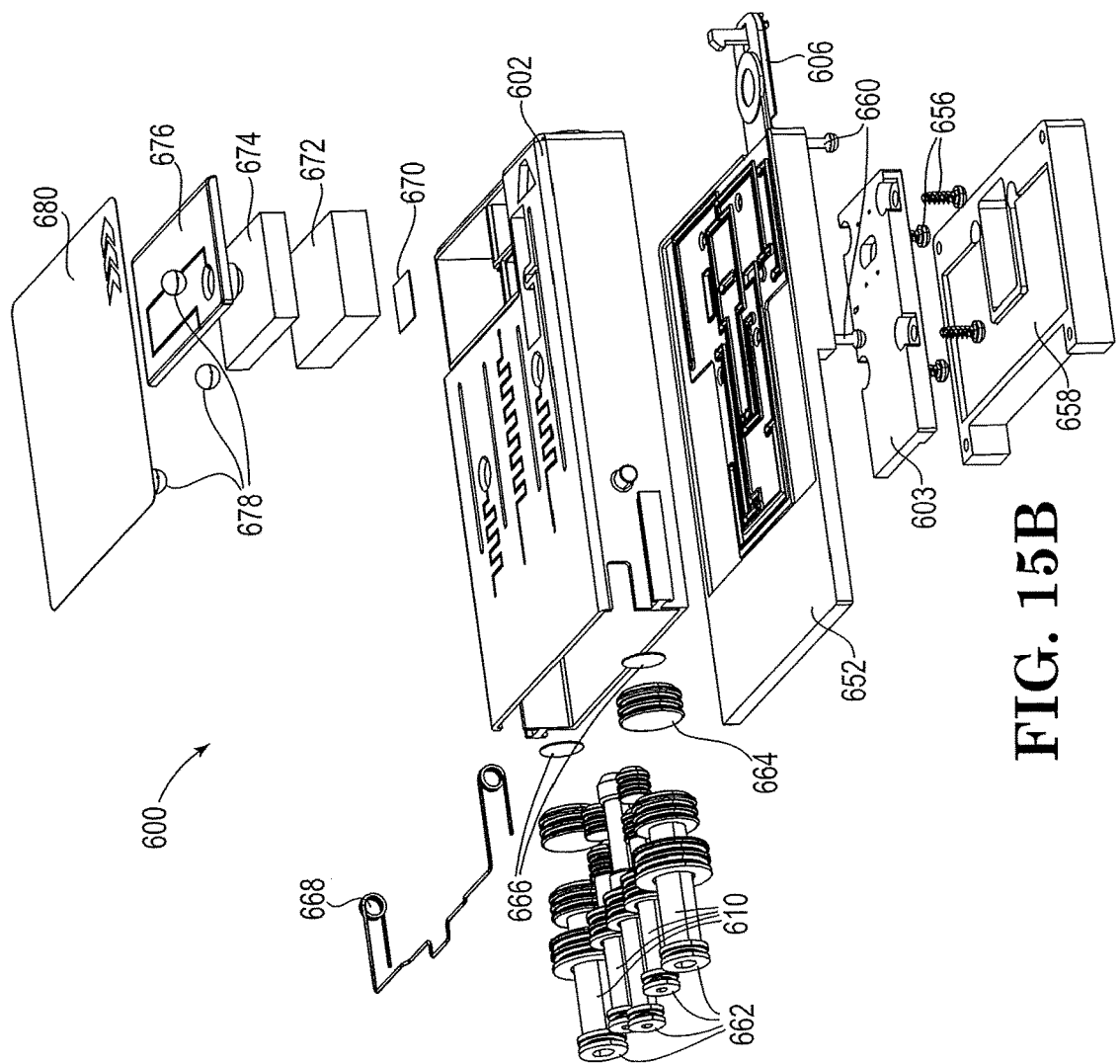
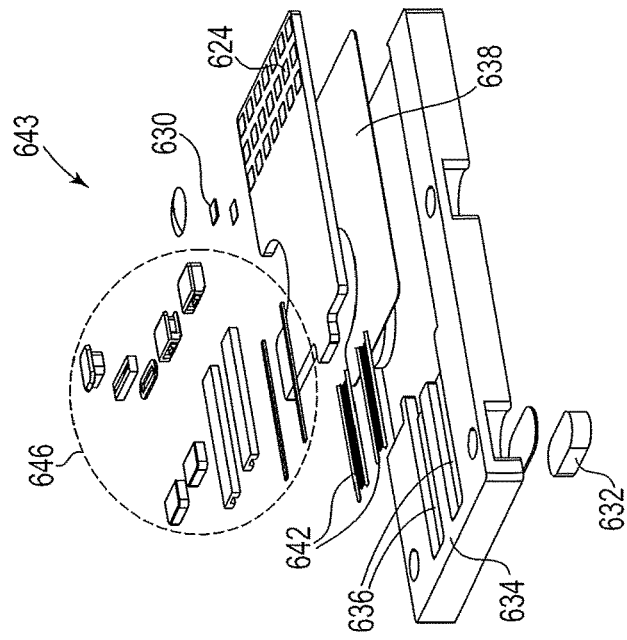
FIG. 15B
FIG. 15A

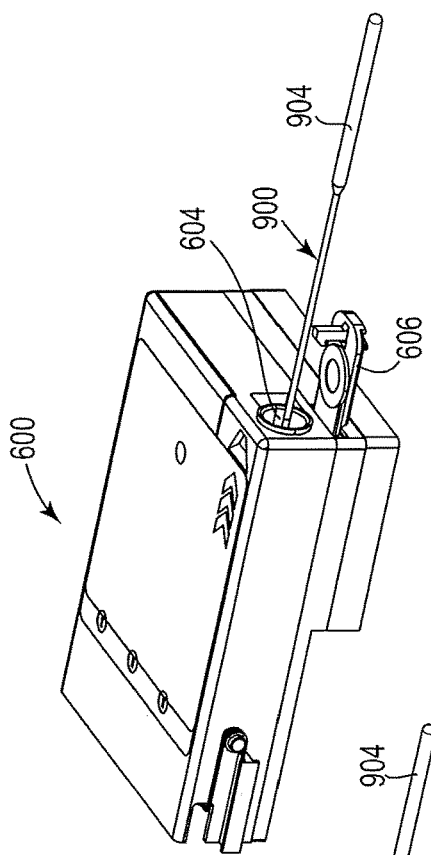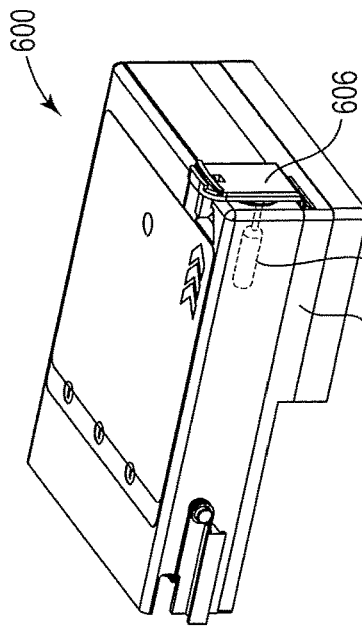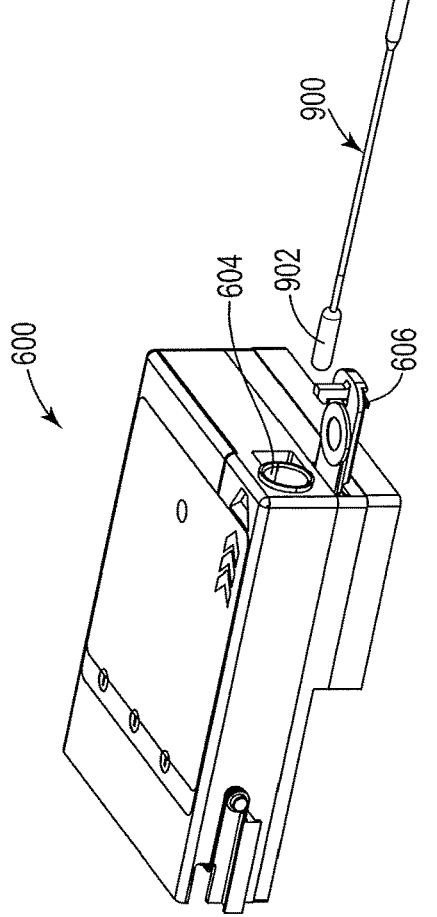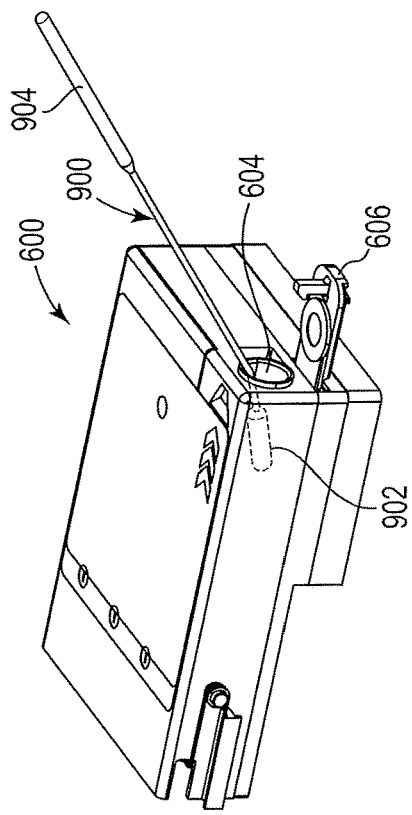

MICROFLUIDIC REACTION CHAMBER FOR AMPLIFICATION OF NUCLEIC ACIDS

BACKGROUND

Microfluidics is a technology that applies across a variety of disciplines including engineering, physics, chemistry, microtechnology and biotechnology. Microfluidics involves the study of small volumes of fluid and how to manipulate, control and use such small volumes of fluid in various microfluidic systems and devices such as microfluidic chips. For example, microfluidic biochips (referred to as "lab-on-chip") are used in the field of molecular biology to integrate assay operations for purposes such as analyzing enzymes and nucleic acids, detecting biochemical toxins and pathogens, diagnosing diseases, etc.

Polymerase chain reaction (PCR) is a powerful tool in the field of molecular biology. This technique allows for replicating/amplifying trace amounts of nucleic acid fragments into quantities that may be analyzed in a meaningful way.

BRIEF DESCRIPTION OF FIGURES

Various examples may be more completely understood in consideration of the following detailed description in connection with the accompanying drawings, in which:

FIGS. 10A-10E illustrate a sectional view of an example plunger as may be implemented in the PCR system of the present disclosure;

FIGS. 11A-11C illustrate a sectional view of an example plunger as may be implemented in the PCR system of the present disclosure;

FIG. 15A is an exploded view of a microfluidic reaction chamber of an example PCR system, according to the present disclosure;

FIG. 15B is an exploded view of an example PCR system into which the microfluidic reaction chamber of FIG. 15A may fit, according to the present disclosure;

FIGS. 18A-18D illustrate perspective views of a method of loading a sample into the cartridge of FIG. 14A, according to the present disclosure;

Figure 1:
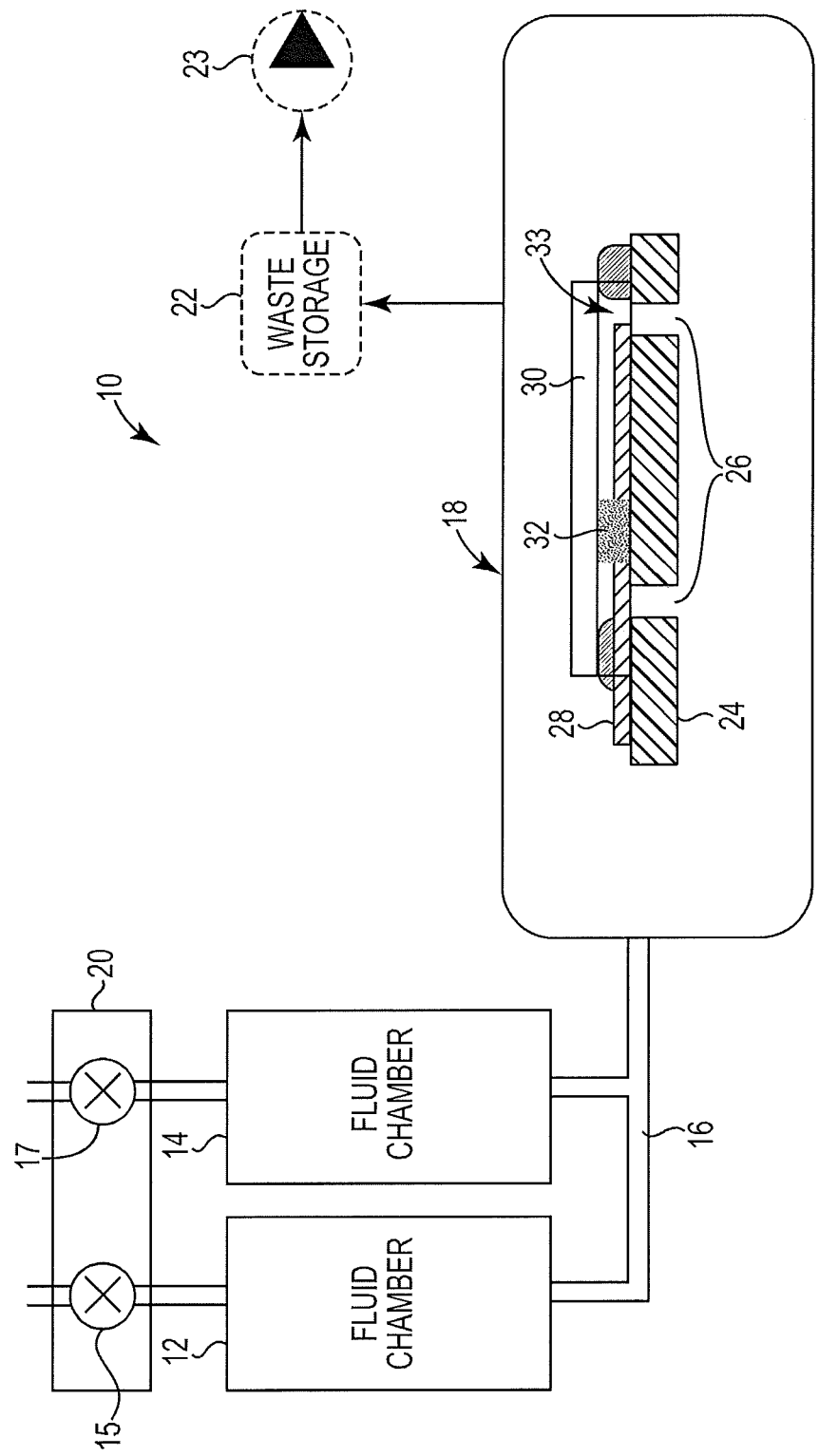
FIG. 1 is a schematic diagram of an example PCR system including a microfluidic reaction chamber, according to the present disclosure.

While various examples discussed herein are amenable to modifications and alter forms, aspects thereof have been shown by way of example in the drawings and will be described in detail. It should be understood, however, that the intention is not to limit the disclosure to the particular examples described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION

Aspects of the present disclosure are believed to be applicable to a variety of different types of apparatuses, systems and methods involving amplification of nucleic acids. In certain implementations, aspects of the present disclosure have been shown to be beneficial when used in the context of PCR. While not necessarily so limited, various aspects may be appreciated through the following discussion of non-limiting examples which use exemplary contexts.

Aspects of various examples disclosed herein are directed to an apparatus including a microfluidic reaction chamber including a reaction-chamber circuit to process a reagent and a biologic sample for amplification of nucleic acids included in the biologic sample. The apparatus further includes a plurality of capillaries to pass the reagent and the biologic sample through the microfluidic reaction chamber. Each of a plurality of valves may be respectively disposed in different ones of the plurality of capillaries, and a valve control system may selectively control each of the plurality of valves. During operation, valve control system may cause the reagent and the biologic sample to selectively move through the microfluidic reaction chamber for the amplification of the nucleic acids according to a particular timing sequence. In various examples, a trapping region disposed in the microfluidic reaction chamber secures the nucleic acids in the microfluidic reaction chamber for amplification using the reaction-chamber circuit. Accordingly, in the following description various specific details are set forth to describe specific examples presented herein. It should be apparent to one skilled in the art, however, that one or more other examples and/or variations of these examples may be practiced without all the specific details given below. In other instances, well known features have not been described in detail so as not to obscure the description of the examples herein. For ease of illustration, the same reference numerals may be used in different diagrams to refer to the same elements or additional instances of the same element. Also, although aspects and features may in some cases be described in individual figures, it will be appreciated that features from one figure or example may be combined with features of another figure or example even though the combination is not explicitly shown or explicitly described as a combination.

Polymerase chain reaction (PCR) is a method used in molecular biology to make many copies of a nucleic acid segment. Using PCR, a single copy (or more) of a nucleic acid sequence is exponentially amplified to generate thousands to millions or more copies of that particular nucleic acid segment. PCR is a temperature-mediated process involving cycling a reaction volume, or mixture, between set temperatures. The reaction volume/mixture contains one or more nucleic acid(s) to be amplified, which is termed the "template" strand. In the reaction volume, the template strand may be in a double-strand form with its complementary strand. If the template and complimentary strands are present as a double-strand nucleic acid molecule, such as a deoxyribonucleic acid (DNA) double helix, this double-strand molecule is denatured in a first step of PCR. In such a process, the double-strand nucleic acid molecule is split into two single nucleic acid strands. In this first step of PCR, the two strands of a double-stranded molecule are physically separated at a high temperature in a process called denaturation or melting. Denaturation occurs at a temperature, which is termed the denaturing temperature. The reaction volume/mixture further contains at least two primers. "Primers" refer to or include short single-strand nucleic acid segments, which are also known as oligonucleotides, with sequences that are either partially or entirely complementary to the template (target) nucleic acid sequence. One of the primers is termed a forward primer while the other is termed a reverse primer.

In the second step of PCR, the temperature of the volume/mixture is lowered, and the primers "anneal" (hybridize, or bind), to their complementary sequences on the target nucleic acid sequence. The two, now double-stranded, nucleic acid strands then become templates for an enzymatic reaction using a polymerase to replicate/synthesize/assemble a new nucleic acid strand from free nucleotides that are also found in the reaction volume/mixture. The forward primer hybridizes to a sequence in the sense strand while the reverse primer hybridizes to a sequence in the antisense strand. The hybridization of the primers with the complementary sequences of the sense or antisense strand is termed annealing. This second step takes place at a temperature termed the annealing temperature.

The reaction volume/mixture further contains a polymerase enzyme. In a third step, the polymerase synthesizes a copy of the complement starting from the forward primer and synthesizes a copy of the sense strand starting from the 5' end of the reverse primer. Throughout the synthesis, the copy of the antisense strand also hybridizes with the sense strand and the copy of the sense strand hybridizes with the antisense strand. This third step is termed elongation and is carried out at a temperature called the elongation temperature. After the elongation step, the first, second, and third steps are repeated until the extent of amplification is achieved, wherein multiple copies of the sense and antisense strands are made. As PCR progresses, the nucleic acid generated is itself used as a template for replication, setting in motion a chain reaction in which the original nucleic acid template is exponentially amplified.

During PCR, the denaturing temperature is chosen such that the single strands of the nucleic acid denature while not effecting, e.g., damaging, the polymerase. An example denaturing temperature is about 95 degrees C. The annealing temperature may depend on the sequence and length of the primers. An example annealing temperature is between about 50 degrees C. and 65 degrees C. The elongation temperature may depend on the polymerase enzyme used. For example, if using Taq DNA polymerase, an elongation temperature of about 72 degrees C. may be used. After elongation, the temperature is returned to 94 degrees C. for denaturation of the double-stranded DNA to single-stranded DNA. This cycling from denaturation-annealing-elongation is repeated a number of times, such as over 20 to 40 cycles.

As discussed above, several components and reagents may be used in PCR. Among these components are, a biologic sample that contains the target sequence(s) to be amplified, an enzyme that polymerizes new nucleic acid strands, two (or more) nucleic acid primers, such as deoxyribonucleotide triphosphates (dNTPs) and, and a buffer solution providing a suitable chemical environment for amplification and optimum activity and stability of the polymerase. Examples of the polymerase enzyme include, but are not limited to, DNA polymerase such as Taq DNA polymerase, and reverse transcriptase. Examples of the buffer solution include components such as bivalent cations, including magnesium (Mg) or manganese (Mn) ions and monovalent cations, such as potassium (K) ions, among others. Further, PCR may include reporter molecules such as fluorophores or molecules that generate an electrochemical signal. Together, these components are commonly known in the art simply as "master mix" and form the environment conducive to nucleic acid amplification.

In various examples of the present disclosure, the method of nucleic acid amplification generally includes the steps of contacting the reaction volume/mixture containing a nucleic acid template with an adsorption material, such as paramagnetic beads. Non-limiting examples of such paramagnetic beads may include DYNABEADS MYONE Silane, M-280 from THERMOFISHER SCIENTIFIC INC., and DYNABEADS MYONE Silane, M-450 from THERMOFISHER SCIENTIFIC INC. Instead of using Peltier heaters or infrared lamps to transfer heat to the vessel containing the reaction mixture, the reaction of the present disclosure may be heated to the appropriate temperature for PCR using a reaction-chamber circuit in the microfluidic reaction chamber.

The present disclosure relates to an improved system for conducting PCR. Particularly, the present disclosure relates to a system and/or cartridge in which a microfluidic reaction chamber receives the components for PCR in an ordered sequence via a valve/capillary valve system, for example. A series of controlled valve sequences release the components, such as buffer, a biologic sample, and a reagent such as master mix, among others, into the microfluidic reaction chamber, where the PCR reaction is performed. The microfluidic reaction chamber itself may provide the heat to perform PCR, and sensors may be disposed within the chamber to detect, in real time or near real-time, the amplification of nucleic acids. In various embodiments, a pump such as a thermal inkjet pump as a non-limiting example, may be used to pull/push the fluid components through the capillaries and through the microfluidic reaction chamber. Additionally, in various embodiments the nucleic acids from the biologic sample may be secured within the reaction chamber, such as with the use of paramagnetic beads.

The nucleic acids capable of being amplified using the present invention include, but are not limited to DNA which may be single-stranded, double-stranded, linear, covalently closed, supercoiled and relaxed circular forms, or RNA which may be single stranded, double stranded, linear or covalently closed, or a combination of DNA and RNA. Further, nucleic acids capable of being amplified using the present invention may include any form of DNA or RNA (e.g. chromosomal or mitochondrial DNA, cell free DNA, ribosomal RNA, mRNA, either intact or fragmented, etc.) and from any source (e.g. viral, prokaryotic, eukaryotic, or archaeal, etc.), whether naturally occurring or synthetically generated.

Turning now to the figures, and particularly to FIG. 1, this figure provides a schematic diagram of an example PCR system including a microfluidic reaction chamber, according to the present disclosure. Particularly, FIG. 1 illustrates some components of an example PCR system 10. As illustrated, the system 10 includes a microfluidic reaction chamber 18 including a reaction-chamber circuit 28 to process a reagent and a biologic sample for amplification of nucleic acids included in the biologic sample. The system 10 may further include a plurality of capillaries 16, to pass the reagent and the biologic sample through the microfluidic reaction chamber 18. The capillaries 16 may branch, as illustrated in FIG. 1, to couple the microfluidic reaction chamber 18 with various components of system 10. In various examples, a plurality of valves 15, 17, may be disposed in different ones of the plurality of capillaries. Moreover, in some examples, a valve control system 20 may selectively control each of the plurality of valves 15, 17, and, during operation, cause the reagent and the biologic sample to selectively move through the microfluidic reaction chamber 18 for the amplification of the nucleic acids according to a particular timing sequence. Collectively, the capillaries 16, the valves 15, 17, and the valve control system 20 are referred to herein as the capillary valve system. Furthermore, in various examples, a trapping region 32 disposed in the microfluidic reaction chamber 18 may secure the nucleic acids in the microfluidic reaction chamber 18 for amplification using the reaction-chamber circuit 28.

In some examples, system 10 includes a fluid input region that comprises a plurality of fluid chambers, with two fluid chambers, a first fluid chamber 12 and second fluid chamber 14, shown in the example system 10. Although two fluid chambers are illustrated in FIG. 1, it is noted that more or fewer fluid chambers may be used (as discussed further herein). Fluids, or fluid inputs, may be moved from fluid chambers 12, 14 (alternatively known as a fluid input region) through a plurality of capillaries, indicated in FIG. 1 as 16. The fluids may be sequentially released into a microfluidic reaction chamber 18 where a nucleic acid amplification reaction may be performed. A plurality of valves, with a first valve 15 and a second valve 17, shown in the example system 10 may be disposed in different ones of the plurality of capillaries 16. The valves described herein may be actuated passively such as with a bubbler, actively such as with an actuator circuit, or manually, as non-limiting examples.

In some examples, system 10 may include a pump 23 to move a reagent and a biologic sample from the fluidic input region and through the microfluidic reaction chamber 18. The pump 23 may be a thermal inkjet drop ejecting pump, or other bubble-driven inertial micropump, although other suitable pumps or components that may act as a pump are contemplated. The pump 23 is shown located downstream from the microfluidic reaction chamber 18. However, such a pump 23 in the example system 10 may alternatively be located upstream from the microfluidic reaction chamber 18, and may push, rather than pull, fluids through the microfluidic reaction chamber 18. The pump 23 may be disposed on a same or a different side of the microfluidic reaction chamber 18 relative to a side of the microfluidic reaction chamber 18 on which the fluid chambers 12, 14, for example, are disposed. Additionally, in various examples, the pump 23 may terminate a flow of the reconstituted reagent solution from the fluid chambers to the microfluidic reaction chamber when a level of the reconstituted reagent solution in the microfluidic reaction chamber reaches a threshold level. For instance, the microfluidic reaction chamber 18 may include a sensor (not illustrated in FIG. 1) disposed within the microfluidic reaction chamber 18 to detect a level of the level of the reconstituted reagent that is in the microfluidic reaction chamber 18. The sensor can include circuitry to instruct the pump 23 to stop operating responsive to the sensor detecting that the microfluidic reaction chamber 18 has a threshold level of reagent disposed therein.

As discussed further with regards to FIGS. 10A-E, FIGS. 11A-11C, FIGS. 12A-B, and FIGS. 17A-17E, each of the respective fluid chambers 12, 14, may include a respective plunger to expel fluid therein. As an illustration, the first fluid chamber 12, coupled to the plurality of capillaries 16, may include a first plunger (not illustrated in FIG. 1) to mix the biologic sample with a lysis solution, responsive to receipt of the biologic sample. The first fluid chamber 12 may receive the biologic sample, and a first plunger may be actuated to force a lysis solution into the biologic sample. Each of the first plunger and the second plunger may translate a stored volume along a length of the associated chamber until a stop feature in the chamber is reached.

In some examples, the lysis solution may include adsorption beads to bind with nucleic acids of the biologic sample. For instance, the lysis solution may cause lysis of the cellular membranes within the biologic sample, thereby releasing the nucleic acids therein. The lysis solution may further include adsorption beads, such as paramagnetic beads or other microparticles with surface chemistry to bind to nucleic acid molecules, and that may secure and/or isolate the nucleic acids within the microfluidic reaction chamber 18. In such non-limiting examples, the system 10 may include a magnet external to the reaction-chamber circuit 28 to secure the adsorption beads within the microfluidic reaction chamber 18.

The second fluid chamber 14, coupled to the plurality of capillaries 16, may include a lyophilized reagent solution and a second plunger (not illustrated in FIG. 1) to allow a buffer to mix with the lyophilized reagent solution when depressed beyond a threshold within the second fluid chamber 14 and form a reconstituted reagent solution. a second fluid chamber to receive the reagent, the second fluid chamber coupled to a second plunger actuated to force a reconstitution buffer into the reagent As discussed herein, the valve control system 20 can selectively move the biologic sample with the lysis solution (from the first fluid chamber 12) and the reconstituted reagent solution (from fluid chamber 14), through the microfluidic reaction chamber 18 according to the particular timing sequence. While the above describes the first fluid chamber 12 including the lysis solution and the biologic sample, and the second fluid chamber 14 including the buffer and the lyophilized reagent solution, it is contemplated that either chamber may receive and/or store the described volumes.

A waste storage chamber 22 is also shown in system 10 that may hold waste or remaining portions of the fluids (i.e., drive fluid) that are driven through the microfluidic reaction chamber 18. Although termed a waste chamber, it is to be understood that in other examples, the waste storage chamber 22 may include a chamber, channel, passage, conduit, volume, other component, or network thereof.

The fluids introduced from fluid chambers 12, 14 of system 10 may include, but are not limited to, a sample, a biological sample, a lysis buffer, a binding buffer, a reconstitution buffer, and Master mix, for example. One example sequence for adding the fluids from fluid chambers, such as 12, 14, to the microfluidic reaction chamber 18 may begin with addition of a fluid from a first fluid chamber 12, which may be a sample with cells suspended therein, to be evaluated, such as blood, sputum, urine, tissue, fecal matter, etc., or may be a swab of cells, or cells suspended in a buffer, or another fluid, for example. The first fluid chamber 12 may also include a reagent, or more than one reagent, for example, that may be added to the sample in order to extract nucleic acids from a target organism in the sample, for example, prior to the sample being driven through the microfluidic reaction chamber 18. As such, the sequence may involve actuating a first plunger within a first fluid chamber 12 of a nucleic acid amplification cartridge to mix a lysis solution with a biologic sample disposed therein. The reagent or reagents may include a chemical lysis solution to disintegrate or otherwise break down cellular membranes encapsulating the nucleic acids. Alternatively, target organisms may be lysed using other methods, such as thermal or mechanical methods (e.g., ultrasonic).

Next, fluid from a second fluid chamber 14, which may include master mix, for example, may be driven through the microfluidic reaction chamber 18. The master mix may be dry (e.g., lyophilized) and may be reconstituted with a buffer before being driven or pumped through the microfluidic reaction chamber 18. As such, the sequence may involve actuating a second plunger within a second fluid chamber of the nucleic acid amplification cartridge to mix a lyophilized reagent solution (e.g., master mix) with a buffer solution disposed therein.

Other additional or alternative fluids may be driven through the microfluidic reaction chamber 18. An example of such a fluid is a wash buffer. The purpose of any suitable wash buffer may be to wash away any remaining components from within the microfluidic reaction chamber 18 that may interfere with PCR or detection of nucleic acids, for example. The wash buffer then may continue on through system 10 to the waste storage chamber 22, and may carry any remaining waste components in the microfluidic reaction chamber 18 during PCR, for example.

The sequence may further include pumping, such as using a bubble-driven inertial micropump, a first volume from the first fluid chamber 12 and a second volume from the second fluid chamber 14 through a microfluidic reaction chamber 18 of the nucleic acid amplification cartridge according to a particular timing sequence. The sequence in which each of the volumes is driven into the microfluidic reaction chamber 18 may be particular to performance of PCR, for example. The fluids or fluid inputs may be released into the microfluidic reaction chamber 18 in different suitable sequences by a series of controlled valve and/or pump sequences, for example. For instance, the sequence may include actuating a first valve 15 disposed in a capillary 16 coupling the first fluid chamber 12 and the microfluidic reaction chamber 18, to dispense the first volume in the microfluidic reaction chamber 18 and actuating a second valve 17 disposed in a capillary 16 coupling the second fluid chamber 14 and the microfluidic reaction chamber 18, to dispense the second volume in the microfluidic reaction chamber 18. Other suitable methods of moving the fluids or fluid inputs are also contemplated.

In system 10 in FIG. 1, a sectional view of one example microfluidic reaction chamber 18 is illustrated, although other configurations or examples of microfluidic reaction chambers are also contemplated. Some other examples of microfluidic reactions chambers for the example PCR systems are described herein below.

Microfluidic reaction chamber 18 may be formed from a substrate 24 that may include a single or multiple input and output openings 26 extending there through. Fluid may be introduced from beneath the microfluidic reaction chamber 18 using the opening 26 or openings in the substrate 24. In some examples, the substrate 24 may, for example, comprise a silicon-based wafer or may be formed of single crystalline silicon, polycrystalline silicon, gallium arsenide, glass, silica, ceramics, plastics, or a semiconducting material, for example. In some examples, the substrate 24 may be a composite material, and/or include multiple layers of different materials. In some examples, the openings 26 may be formed in the silicon substrate by laser machining and/or chemical etching. The one of the openings 26 may receive the fluid volumes dispensed from the fluid chambers 12, 14, and another one of the openings 26 may dispense the fluid to waste storage 22, as described herein.

The microfluidic reaction chamber 18 may also include a reaction-chamber circuit 28, which may be, for example, a semiconductor chip, as shown. In the example illustrated in FIG. 1, the reaction-chamber circuit 28 is mounted on top of the substrate 24. The presence of the reaction-chamber circuit 28, in the microfluidic reaction chamber 18 may provide the ability to sense or measure properties of components of the fluid in the chamber 18. The reaction-chamber circuit 28 may also provide heat to the fluid in the chamber 18 during the thermal cycle of PCR. As such, the microfluidic reaction chamber 18, via the reaction-chamber circuit 28, may heat the first volume and the second volume from the first and second chambers to amplify nucleic acids of the biologic sample for PCR. The reaction-chamber circuit 28 may be mounted on the substrate 24, or may be suspended in the microfluidic reaction chamber 18 such that multiple sides around the reaction-chamber circuit 28 are in contact with fluid.

A lid 30 may also partially form or make up the microfluidic reaction chamber 18, and may be mounted on the substrate 24, and may be spaced apart from the reaction-chamber circuit 28 providing space, or a via 33, through which the fluid inputs may be driven or pumped. The via 33 may be formed between the lid 30 and the reaction-chamber circuit 28. The lid 30 may comprise glass, quartz, poly (methyl methacrylate), polycarbonates, cyclic olefin copolymer, polyethylene terephthalate, polyethylene terephthalate glycol, and polyvinyl chloride for example, although other suitable materials are also contemplated. Alternatively, input or output openings may be created through the lid 30 rather than, or in addition to, the substrate 24. As such, the microfluidic reaction chamber 18 may include a reaction-chamber circuit 28 on a substrate 24 and a lid 30 disposed over the reaction-chamber circuit 28 to form a via 33 between the lid 30 and the reaction-chamber circuit 28.

The semiconductor chip 28, or reaction-chamber circuit, may include at least one sensor in order to detect amplified nucleic acids, for example, in real time or near-real time during PCR or after PCR is complete. The sensor(s) may be optical sensors and/or electrochemical sensors. The sensors may be suspended in the microfluidic reaction chamber 18 and may face away and/or toward the substrate 24. Additionally and/or alternatively, external optics may be used to identify the presence of amplified nucleic acids, for example, either during PCR or after PCR is complete. Other suitable methods for identifying the presence and/or amount of amplified nucleic acids, for example, are also contemplated. Sensors on the circuit can also be used to sense the presence or absence of each reagent or type of fluid along the circuit and/or chamber, thereby monitoring the whole process.

The system 10 may also include a trapping region 32 that may be disposed in the microfluidic reaction chamber 18 in order to secure nucleic acids in the microfluidic reaction chamber 18 for amplification using the reaction-chamber circuit 28. One example of a material that may comprise a trapping region is a magnet. A magnet (not shown or included in system 10, but included in subsequent described systems) external to the reaction-chamber circuit 28 may secure nucleic acids within the microfluidic reaction chamber. For instance, paramagnetic beads may be introduced and/or mixed with the biologic sample during and/or after lysis of the cellular membranes, for the nucleic acids to adsorb to the paramagnetic beads. The paramagnetic beads may act to retain nucleic acids for example, by binding nucleic acids. For example, the paramagnetic beads may have surface chemistry that encourages nucleic acids to be absorbed onto the beads.

If paramagnetic beads are used as the trapping region 32, a magnet may be used, for example, to retain nucleic acids. The trapping region 32, including paramagnetic beads, for example, may be secured in the via 33 using a magnet (not shown or included in system 10, but included in subsequent described systems) external to the reaction-chamber circuit 28. An alternative to the magnet is a filter. The magnet or filter may be located in system 10 either upstream from the microfluidic reaction chamber 18 in a channel or capillary or within the microfluidic reaction chamber 18, for example.

Although the introduction of fluids or other components, for example, to system 10 is described in a particular sequential order, it is contemplated that the example fluids or components may be introduced in any suitable order. Also, in system 10, or any example system disclosed herein, suitable components, other than those described, that function in the example systems are also contemplated. The disclosure is not limited to the particular components disclosed herein.

Figure 2:
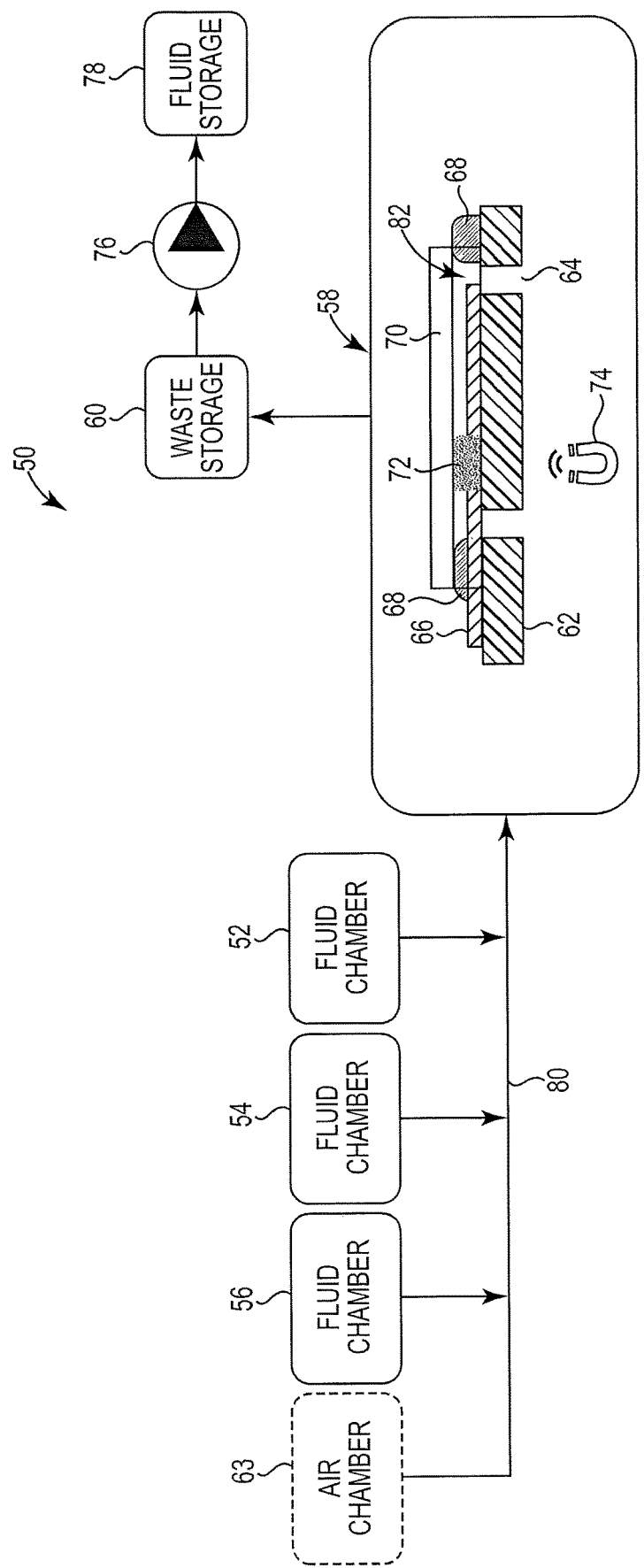
FIG. 2 is a schematic diagram of an example PCR system including a microfluidic reaction chamber, according to the present disclosure.

FIG. 2 shows a schematic view of an example PCR system 50. The description of the parts or components of system 10 above applies to corresponding parts in system 50. In system 50, however, three fluid chambers 52, 54, 56 are shown. The fluid inputs in the fluid chambers (first, second and third, respectively) 52, 54, 56 may be added in any suitable order for PCR, however, an example sequence will be described. The fluids or fluid inputs may be driven or moved through a plurality of capillaries 80 that extend between the fluid chambers 52, 54, 56 and the microfluidic reaction chamber 58.

One example sequence for adding the fluidic inputs to the microfluidic reaction chamber 58 may begin with addition of contents of the first fluid chamber 52, which may be a sample with cells suspended therein, to be evaluated, such as blood, sputum, urine, tissue, fecal matter, etc., or may be a swab of cells, or cells suspended in a buffer, or another fluid, for example. The fluid input of the first fluid chamber 52 may also include a reagent, or more than one reagent, for example, that is to be added to the sample in order to extract nucleic acids from a target organism in the sample, for example, prior to the sample being driven through the microfluidic reaction chamber 58. An example of such a reagent is a lysis solution.

A second fluid input in second fluid chamber 54 may next be driven through the microfluidic reaction chamber 58. An example of such a fluid input is a wash buffer. The purpose of a suitable wash buffer may be to wash away any remaining components from within the microfluidic reaction chamber 58 that may interfere with PCR or detection of nucleic acids, for example. The wash buffer then may continue on through system 50 to a waste storage chamber 60, and may carry away remaining waste components from the microfluidic reaction chamber 58 during PCR, for example.

Next, a third fluid input located or stored in third fluid chamber 56, including master mix, for example, may be driven through the microfluidic reaction chamber 58. The Master mix may be dry (e.g., lyophilized) and reconstituted with a buffer before being driven or pumped through the microfluidic reaction chamber 58, or a liquid Master mix may be added.

Optionally, another input may be moved through the microfluidic reaction chamber 58 and may be introduced through an optional input 63. An optional component used in PCR that may be introduced may be air.

In system 50 illustrated in FIG. 2, a sectional view of an example microfluidic reaction chamber 58 is illustrated. Microfluidic reaction chamber 58 may be formed from a substrate 62 that may include a single or multiple input or output openings 64 extending there through. Fluid may be introduced from beneath the microfluidic reaction chamber 58 using the opening 64.

The microfluidic reaction chamber 58 may also include, or have disposed within, a reaction-chamber circuit 66, such as a semiconductor chip. In the example illustrated in FIG. 2, the reaction-chamber circuit 66 is mounted on top of the substrate 62.

A lid 70 may also partially form or make up the microfluidic reaction chamber 18, and may be mounted on the substrate 62 to form a via 82 between the lid 70 and the reaction-chamber circuit 66. The fluid inputs may run or be driven through the via 82. The lid 70 may be attached to the substrate 62 with multiple adhesive portions 68, or any other suitable attachment means. The adhesive portions 68 shown may comprise a sealing adhesive or any other suitable adhesive.

The system 50 may include a trapping region 72 that may be disposed in the microfluidic reaction chamber 58 in order to secure nucleic acids in the microfluidic reaction chamber 58 for amplification using the reaction-chamber circuit 66. The trapping region 72 may comprise paramagnetic beads and/or a magnet 74. The magnet 74 may be included, as shown, in order to retain nucleic acids in a specified location by selective placement of the magnet 74. The reconstituted Master Mix® component that may be driven through the microfluidic reaction chamber 58 acts to elute nucleic acids off the paramagnetic beads in the trapping region 72, so that the nucleic acids can be detected.

In the example system 50, a pump 76 may be used to move fluid from fluid chambers 52, 54, and 56 and through the microfluidic reaction chamber 58. The pump 76 may be a thermal inkjet drop ejecting pump, for example. The pump 76 is shown located downstream from the microfluidic reaction chamber 58, although may, alternatively, be located upstream. Also shown is an ejected drive fluid storage chamber 78, which is located downstream from the pump 76.

An example method of performing rapid PCR may be explained with regards to FIG. 2. A sample may be inserted into fluid chamber 52. A reagent, such as a lysis/binding buffer, or another suitable reagent or reagents may be introduced to the sample in fluid chamber 52 to extract nucleic acids from a target organism in the sample. The fluid chamber 52 may also contain paramagnetic beads, for example, and the nucleic acids may be bound to the microbeads. The reagent may hold the microbeads using surface chemistry, working with the chemistry of the liquid reagent, and may encourage nucleic acids to be adsorbed onto the microbeads. The reagent may also include a chemical lysing agent that may release nucleic acids out of the biologic sample. Alternatively or additionally, external heat and/or mechanical forces may be applied to the reagent and sample in order to help lyse the cellular membranes. In second fluid chamber 54, a lyophilized master mix may be reconstituted with a reconstitution buffer.

The lysed sample in fluid chamber 52 with DNA bound onto paramagnetic beads, or microbeads, are then pumped through the microfluidic reaction chamber 58, using the pump 76. The microbeads with DNA are trapped in the chamber 58, while other components continue to waste storage 60. Next, the reconstituted master mix is pumped into the microfluidic reaction chamber 58. The reaction-chamber circuit 66 may then detect when this process is complete. Once that happens, PCR is performed to amplify the nucleic acids contained within the microfluidic reaction chamber 58. For instance, the reaction-chamber circuit 66 may provide the heating during thermal cycling of PCR. The presence of the amplified nucleic acids may then be detected with external optics and/or by sensors on the reaction-chamber circuit 66 or elsewhere in the microfluidic reaction chamber 58. Nucleic acids may be detected in real time during PCR or after PCR is complete.

An alternative to paramagnetic beads may be non-magnetic silica or polymer beads, which may be mechanically trapped in the microfluidic reaction chamber 58 with a filtration component at or near an output opening. Alternatively, DNA may be directly adsorbed onto the lid 70, substrate 62, silicon of chamber 58, etc., and may potentially be aided with modified surface chemistry, such as silanol groups, antibodies, or oligonucleotides.

An alternative to lysing the target organism in the sample in fluid chamber 52, for example, is that a sample may be pre-lysed. As another alternation, the sample may be pre-lysed and also pre-bound to beads before being added to the system 50.

Figure 3:
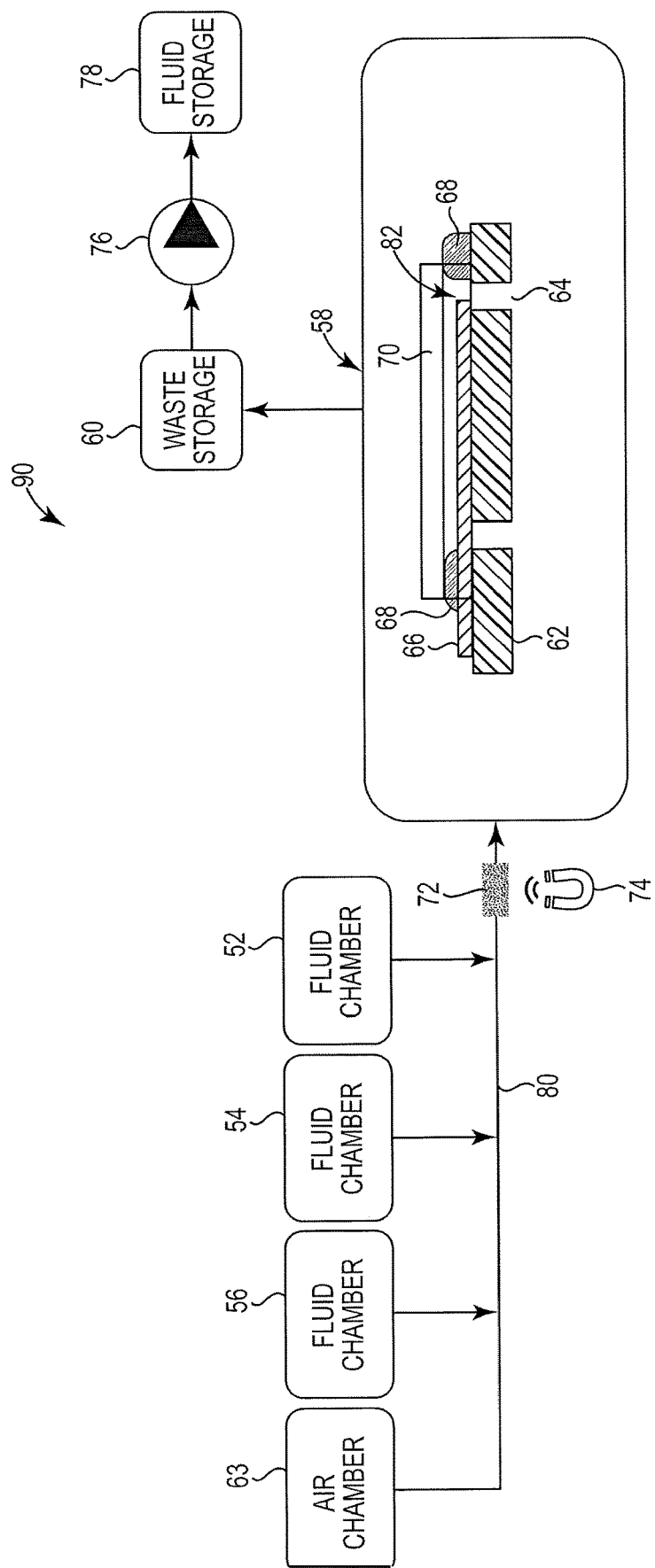
FIG. 3 is a schematic diagram of an example PCR system including a microfluidic reaction chamber, according to the present disclosure.

FIG. 3 shows a schematic view of an example PCR system 90. The system 90 contains the same components as system 50 in FIG. 2, which are numbered accordingly. Description of those same parts or components from system 50 above applies to the corresponding parts in system 90. A difference in system 90 from system 50, however, is the location of the trapping region 72 and the magnet 74. The trapping region 72, which may comprise paramagnetic beads and the magnet 74, are located upstream from the microfluidic reaction chamber 58, in or near the capillaries 80.

Paramagnetic beads that may be introduced to the sample in the first fluid chamber 52 (FIG. 3) may be trapped upstream of the microfluidic reaction chamber 58 instead of inside the chamber 58. The beads may be trapped using a filter or with a magnetic field for paramagnetic beads. Some chemistries may not require heat to elute off nucleic acids from the beads. A change in chemical properties or components in passing liquid, such as pH, may elute the nucleic acids off the beads. Alternatively, the reconstituted master mix may pass through the beads on its way to the microfluidic reaction chamber 58 and may have properties that elute the nucleic acids off the beads and may then transport the nucleic acids to the microfluidic reaction chamber 58.

Figure 4:
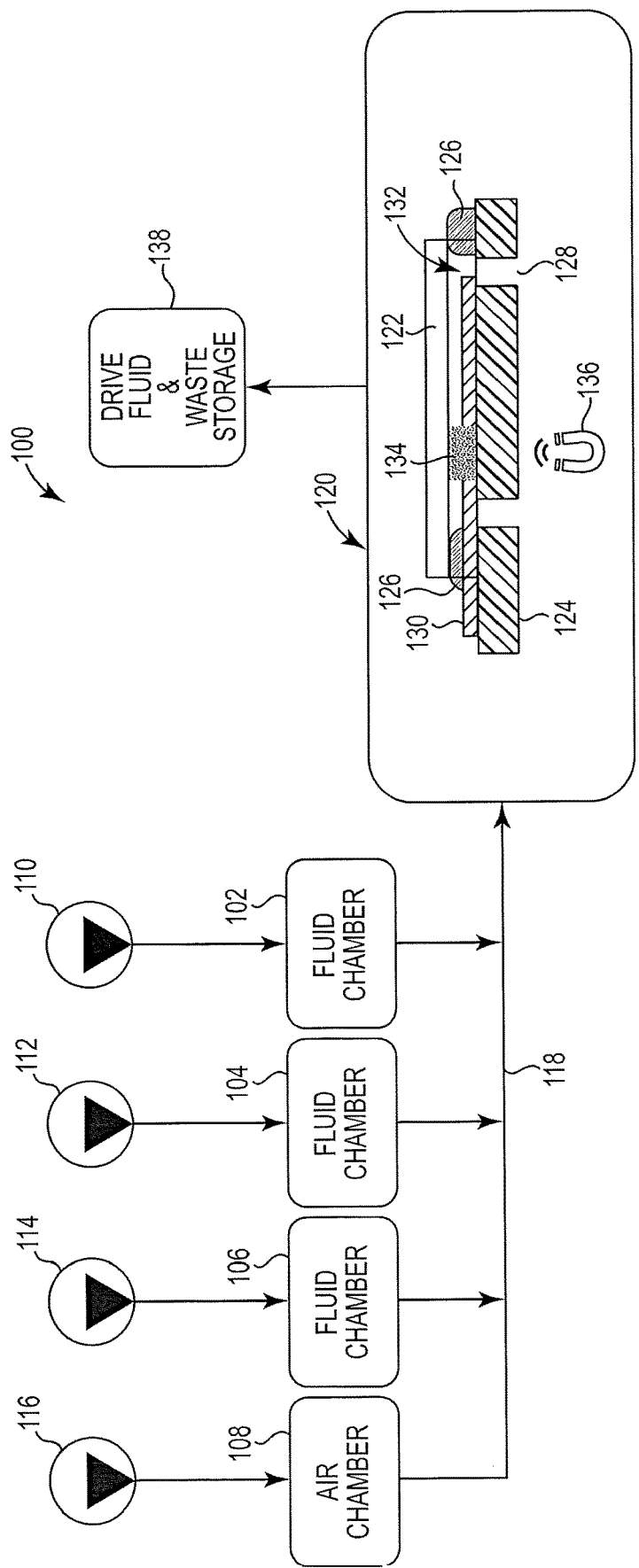
FIG. 4 is a schematic diagram of an example PCR system including a microfluidic reaction chamber, according to the present disclosure.

FIG. 4 shows a schematic view of an example PCR system 100. Similar to systems 50 and 90 in FIGS. 2 and 3 described above, system 100 includes multiple fluid chambers 102, 104, 106, and an optional chamber 108, which may include air, for example. Instead of a pump being located downstream in the system, system 100 includes a plurality of pumps, with a pump 110, 112, 114, and 116 for each of the chambers 102, 104, 106, and 108. The plurality of pumps include, for example, a first pump 110, a second pump 112, a third pump 114, and a fourth pump 116. The pumps 110, 112, 114, 116 may include a pump capable providing a pushing force, including a piezo electric pump, for example. Additionally and/or alternatively, pumps 110, 112, 114, 116 may be thermal inkjet drop ejecting pumps.

The system 100 contains similar components as in systems 50 and 90 in FIGS. 2 and 3. A plurality of capillaries 118 are shown to carry fluid inputs from the chambers 102, 104, 106 and 108. A microfluidic reaction chamber 120 is shown with a lid 122 mounted on a substrate 124, with fluid input/output openings 128, and attached by adhesive portions 126. A reaction-chamber circuit 130 is shown. A via 132 is formed between lid 122 and reaction-chamber circuit 130 through which fluids may be driven in order for a PCR reaction to take place or be performed. A trapping region 134 may include paramagnetic beads and a magnet 136, in which the magnet 136 may be included within or adjacent the microfluidic reaction chamber 120. A drive fluid and waste storage chamber 138 may be included in system 100 downstream from the microfluidic reaction chamber 120. Description of the same parts or components from systems 50 and 90 above applies to the corresponding parts in system 100.

Figure 5:
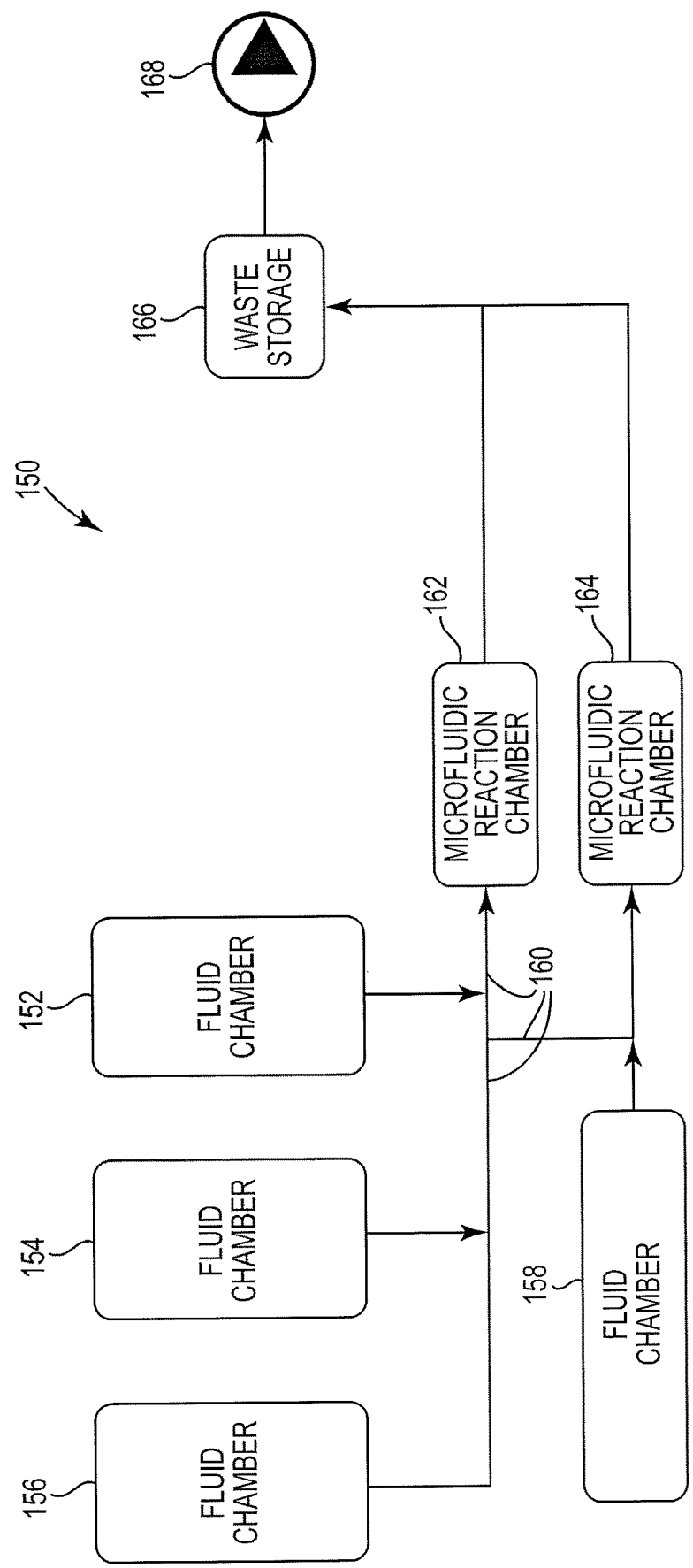
FIG. 5 is a schematic diagram of an example PCR system including a microfluidic reaction chamber, according to the present disclosure.

FIG. 5 shows a schematic diagram of an example PCR system 150 having multiple microfluidic reaction chambers. The description of corresponding components of systems 10, 50, 90 and 100 above applies to those corresponding parts in system 150.

In system 150, four fluid chambers are shown, which are first fluid chamber 152, second fluid chamber 154, third fluid chamber 156 and fourth fluid chamber 158. The fluid chambers 152, 154, 156, 158 are connected by a plurality of capillaries 160 running to two separate microfluidic reaction chambers 162, 164.

In system 150, there are multiple microfluidic reaction chambers, as shown by a first microfluidic reaction chamber 162 and a second microfluidic reaction chamber 164 in FIG. 5. As illustrated, the system 150 may include a second microfluidic reaction chamber including a second reaction-chamber circuit disposed therein, and a second capillary valve system connecting a second fluidic input and the second microfluidic reaction chamber. Although two microfluidic reaction chambers are shown in FIG. 5, other numbers of microfluidic reaction chambers are also contemplated. Both first and second microfluidic reaction chambers 162, 164, as shown, may share some of the same fluid chambers, such as first fluid chamber 152, and second fluid chamber 154, for example. As such, the first microfluidic reaction chamber and the second microfluidic chamber may be coupled to a different respective reagent chamber and a same sample chamber. The first fluid chamber may hold a sample, which may include a lysis/binding buffer. The second fluid chamber 154 may hold a wash buffer, for example. A third and fourth fluid chambers 156, 158 may hold master mix and a reconstitution buffer (or separate components that are mixed prior to being driven through system 150). The lysed sample and wash buffer may be split evenly between the two microfluidic reaction chambers 162, 164. Each microfluidic reaction chamber 162, 164 may be driven in parallel by a common downstream pump 168. Alternatively, an upstream pump or valve system could be used, as described above with regards to system 10. The system 150 may also have a waste storage chamber 166.

Each microfluidic reaction chamber 162, 164 in system 150, however, may have its own Master mix mixture supply, which may be held by third and fourth fluid chambers 156, 158. The separate master mix mixtures allow for each microfluidic reaction chamber 162, 164 to have its own, unique set of nucleic acid targets. This may allow for testing for the presence of multiple organisms in a single sample, for example. In system 150, in order to prevent the master mix mixture intended for the first microfluidic reaction chamber 162 from being transported to the second reaction microfluidic chamber 164, and vice versa, a balanced pressure drop may be applied.

Figure 6:
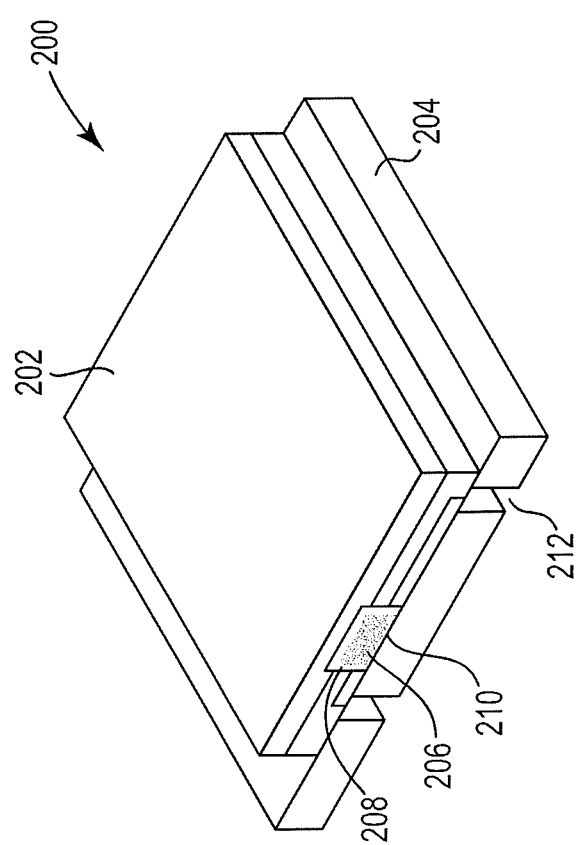
FIG. 6 is a perspective view of an example microfluidic reaction chamber, according to the present disclosure.

FIG. 6 shows a perspective view of an example microfluidic reaction chamber 200 for use in the systems described herein. As shown, a lid 202 may be attached to or mounted on a substrate 204, and may enclose a reaction-chamber circuit 206 in via 208 formed between the reaction-chamber circuit 206 and the lid 202. The via 208 is to allow components, or fluids, in PCR, with such examples as those described above with regards to herein described systems, to flow or be driven through the microfluidic reaction chamber 200. A trapping region 210 is inside the microfluidic reaction chamber 200. Paramagnetic beads, a magnet, and/or a filter may comprise the trapping region 210. For instance, a magnet may be placed. An input/output opening 212 is shown, but other alternative numbers and location for such openings are contemplated. The description of the components of microfluidic reaction chambers in systems shown and described above in FIGS. 1 and 2, for example, apply to the corresponding components in microfluidic reaction chamber 200.

Figure 7:
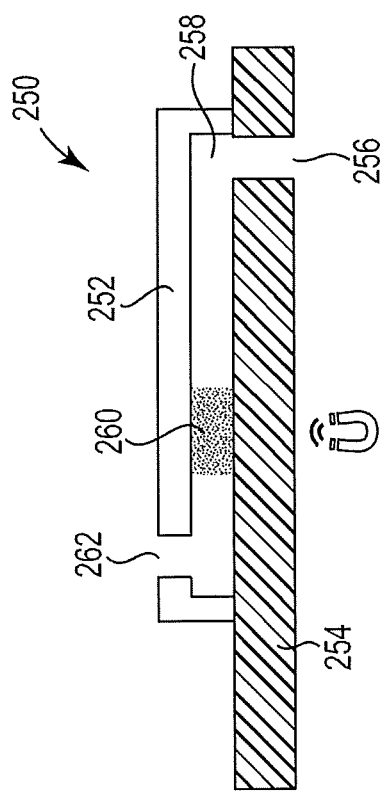
FIG. 7 is a sectional view of an example microfluidic reaction chamber, according to the present disclosure.

FIG. 7 shows a sectional view of a microfluidic reaction chamber 250 that may be included in some of the example systems described herein, or in any other suitable PCR systems. Microfluidic reaction chamber 250 may be formed from a lid 252 mounted or attached to a reaction-chamber circuit 254, or a semiconductor, for example. The reaction-chamber circuit 254 may include a single opening, or, alternatively, multiple input and output openings 256, extending there through. Fluid may be introduced from beneath the microfluidic reaction chamber 250 using input opening 256 in the reaction-chamber circuit 254. Alternatively, an opening 262 or openings in the lid 252 may be used for introduction or outflow of fluid components. A trapping region 260, which may comprise or include paramagnetic beads and a magnet may also be included, as discussed herein. Via 258 may be a space or opening between the lid 252 and the reaction-chamber circuit 254, for example.

Figure 8:
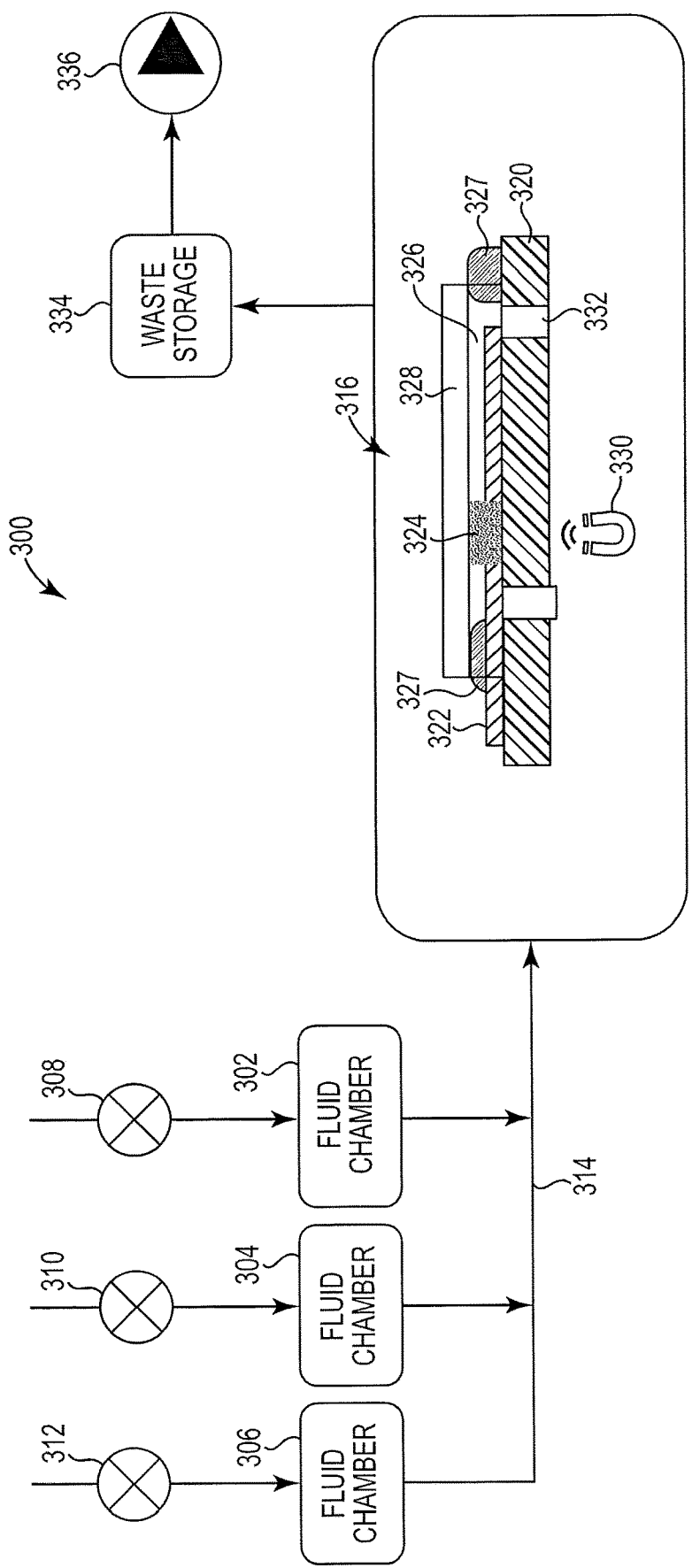
FIG. 8 is a schematic diagram of an example PCR system including a microfluidic reaction chamber, according to the present disclosure.

FIG. 8 shows a schematic view of an example PCR system 300. The description of the parts or components of systems above apply to corresponding parts in system 300. In system 300, three fluid chambers 302, 304, 306 are shown, but other numbers of fluid chambers are contemplated. The fluid inputs within the fluid chambers (first, second and third, respectively) 302, 304, 306 may be added in any suitable order for PCR. The fluids or fluid inputs may be driven or moved through a plurality of capillaries 314 that extend between the fluid chambers 302, 304, 306 and a microfluidic reaction chamber 316. The fluid or fluid inputs in chambers 302, 304, 306 may be released or driven into microfluidic reaction chamber 316 by first, second, and third valves 308, 310, 312 that are open to the atmosphere and may be sequenced to be opened and closed, and are located upstream. The fluid inputs may be driven by a pump (illustrated in the discussion related to FIG. 1). The remainder of the system 300, including the microfluidic reaction chamber 316, may include similar components to those in other systems described herein. The microfluidic reaction chamber 316 includes a lid 328 attached or mounted to a substrate 320, with a reaction-chamber circuit 322 mounted to the substrate 320. The lid 328 and reaction-chamber circuit 322 form a via 326 there between through which fluid inputs may be driven. A trapping region 324 is located within the microfluidic reaction chamber 316, and a magnet is shown 330. A waste storage chamber 334 is located downstream from the microfluidic reaction circuit 316. Adhesive 327 may secure the lid 328 to the substrate 320, as discussed herein. Yet further, the fluid may be driven from the chambers 302, 304, 306 using a pump 336.

In an example microfluidic reaction circuit, the microfluidic reaction chamber may be formed from a lid mounted or attached to a substrate and to a reaction-chamber circuit, or semiconductor chip, for example, which is embedded, or partially embedded, in a portion of the substrate. The reaction-chamber circuit may be over molded by fabrication of the substrate. Embedding the reaction-chamber circuit in the substrate may eliminate the use of the adhesive attachment (e.g., 327 illustrated in FIG. 8) of the reaction-chamber circuit to the substrate.

Figure 9:
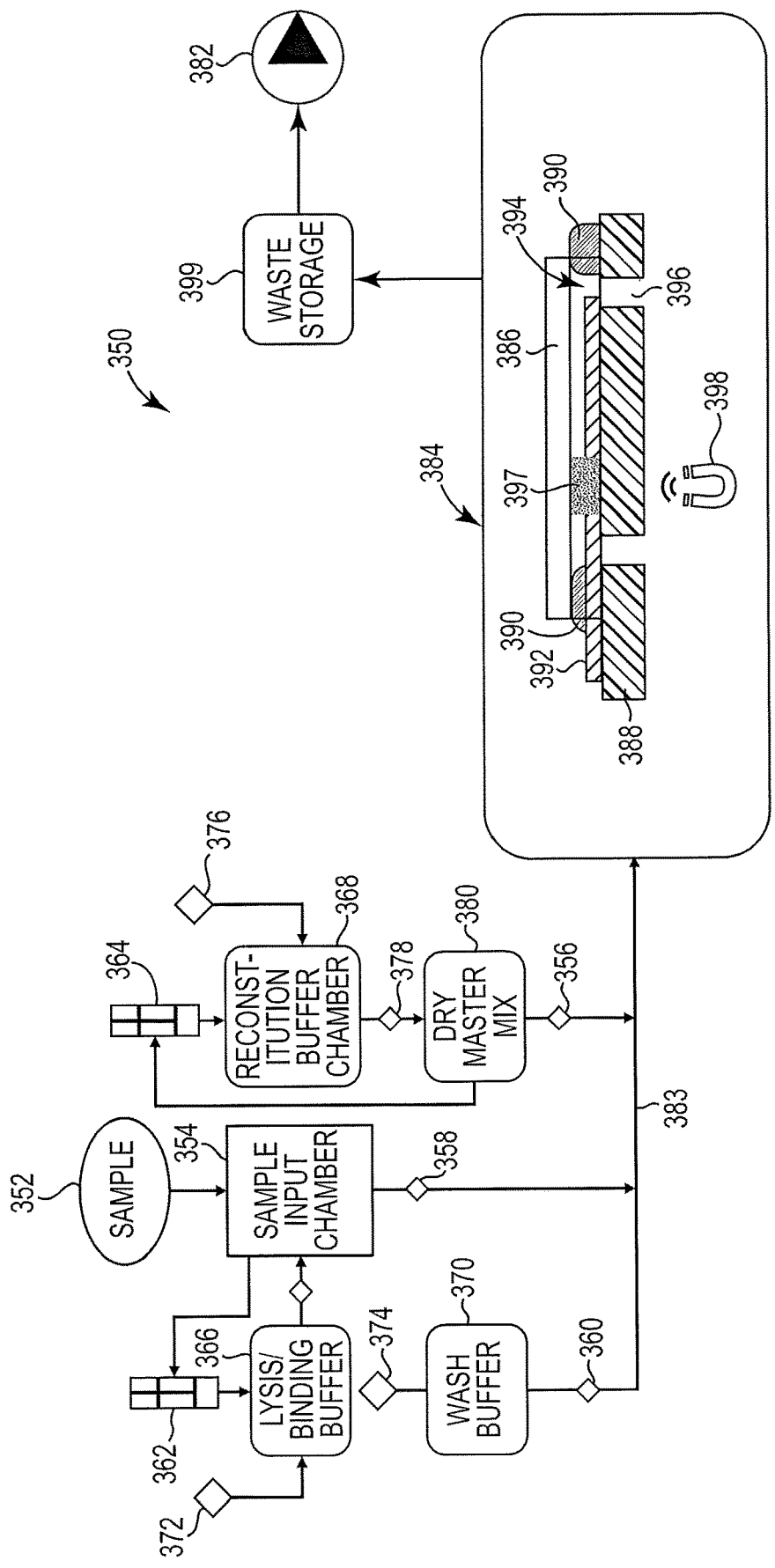
FIG. 9 is a schematic diagram of an example PCR system including a microfluidic reaction chamber, according to the present disclosure.

FIG. 9 shows a schematic view of an example PCR system 350. In system 350, a sample 352 is inserted into a sample input chamber 354. As described herein above, the sample may be, for example, a swab, blood, urine, sputum, tissue, saliva, feces, etc. When the sample input chamber 354 is closed, or self-sealed after sample insertion, internal sealing valves 356, 358, 360 may either be opened or closed as necessary. A first plunger 362 and a second plunger 364 may then be actuated in parallel or sequentially. The first plunger 362 may be actuated in order to force lysis/binding buffer from a lysis/binding buffer chamber 366 into sample input chamber 354. The second plunger 364 may be actuated in order to force reconstituted buffer from a reconstituted buffer chamber 368 to mix with lyophilized master mix in a chamber 380 holding master mix, and to load wash buffer from a wash buffer chamber 370 into the fluid network of the system 350. Sealing valves, 356, 358, 360, sequencing valves 372, 374, 376 and bypass valve 378 can be actuated in parallel or sequentially by the same motion in a mechanism, for example, to expel fluid into the microfluidic reaction chamber 384 for PCR. A description of how the plungers 362, 364 may translate stored liquid is described in more detail below with regard to FIGS. 10A-E.

As an alternative to chemical lysing, other lysing may be performed in system 350. Some examples include, but are not limited to, lysing by heat, and mechanical lysing such as by ultrasonic displacement of the sample, among other examples.

In system 350, a downstream pump 382, pulls the lysed sample through a plurality of capillaries 383 and a microfluidic reaction chamber 384. The pump 382 may be a thermal inject drop ejecting pump, or a piezo pump, for example. The microfluidic reaction chamber 384 may include any of those described herein or suitable alternatives to those described herein. In microfluidic reaction chamber 384, a lid 386 is mounted onto a substrate 388 using adhesive portions 390, although other methods of mounting are contemplated. A reaction-chamber circuit 392 may be at least partially enclosed by lid 386 and substrate 388, leaving a via 394 there between to allow lysed sample and buffer mixture, through the microfluidic reaction chamber 384. An input/output opening 396 may be used to allow the lysed sample and buffer mixture to flow into the via 394.

A trapping region 397 may be included in the microfluidic reaction chamber 384, and may include features to secure nucleic acids within the microfluidic reaction chamber 384, for example. As a non-limiting example, paramagnetic beads may bind to nucleic acids that are trapped by a magnetic field produced by a magnet 398 that is in close proximity to the trapping region 397. The remainder of the fluid and components continue through system 350 to a waste chamber 399.

The pump 382 may also pull a wash buffer through the microfluidic reaction chamber 384 in order to purge the microfluidic reaction chamber 384 of components that may interfere with a nucleic acid amplification reaction or nucleic acid detection, for example. However, some wash buffers may interfere with nucleic acid amplification, such that additional heat from the reaction-chamber circuit 392 may accelerate evaporation and subsequent vaporized wash buffer.

Sequencing of actuation of system 350 may, for example be accomplished by programming actuation of sequencing valves 372, 374, 376 upstream of each branch of a fluid input region of system 350. The three branches of the fluid input region are the branches shown in FIG. 9 including a first branch that includes the chamber and capillaries associated with the sample/lysis buffer chamber 366 and the sample input chamber 354, a second branch that includes the chamber and capillaries associated with the reconstitution buffer chamber 368 and regent chamber 380, and a third branch that includes the chamber and capillaries associated with the wash buffer chamber 370. The sequencing valves 372, 374, 376 may be programmed to allow air in the system 350. A difference in capillary bubble ingestion pressure for each branch, paired with high capillary bubble pressure orifices (e.g., filter), may act as a flow stop that allows the next branch in a sequence to start.

The downstream pump 382, also pulls reconstituted master mix into the microfluidic reaction chamber 384. There may be at least one sensor (not shown) in the microfluidic reaction chamber 384, such as on the reaction-chamber circuit, that may detect when the microfluidic reaction chamber 384 is full of Master mix, which then signals the downstream pump 382 to stop. The microfluidic reaction chamber 384 may hold 1-10 microliters of fluid, for example. Upon reaching a threshold volume of master mix and/or threshold volume of fluid within the microfluidic reaction chamber 384, the pump 382 may stop pulling reconstituted master mix into the microfluidic reaction chamber 384.

Reporter molecules for nucleic acid amplification may be sensed optically or electrochemically, for example by sensors in the microfluidic reaction chamber, in real time or near-real time. The sensors may be located on a semiconductor chip, or reaction-chamber circuit. Additionally and/or alternatively, reporter molecules may be sensed optically off-board or off-chip, meaning the sensor is not located on the reaction-chamber circuit. For example, the reporter molecules may be sensed optically through a glass lid, which may similar in composition and design to lid 386.

FIGS. 10A-E show an example plunger 400 for reconstitution of a lyophilized reagent, and how the plunger 400 may function in a PCR system, such as the system 350 of FIG. 9, for example. FIG. 10A labels the components of the plunger 400 and reagents or fluids that may be in the plunger 400. Starting at the top of plunger 400, a plunger rod 402 extends from outside the top of the plunger 400, through a rod seal 404, which seals contents of the plunger 400, to inside the plunger 400. The bottom end, being inside the plunger 400 of the plunger rod 402, contains a plunger stopper 406, which may push on some reagent or other fluids in the plunger 400. The plunger stopper 406 may have a suitable diameter that allows the plunger stopper 406 to fit and yet slide against the inner cylinder wall 424 of the plunger 400.

Between plunger stopper 406 and a bypass stopper 410, which also fits against the inside wall of the plunger, is a reconstitution buffer 408, for example. The plunger 400, however, is contemplated to contain other reagents or fluids. Below the bypass stopper 410 is a bypass feature 412. A lyophilized reagent 414 may be located below the bypass feature 412 in lower chamber 422. An output opening 416 may be at or near the bottom of plunger 400. An air exchange channel 418 may extend between the lower portion of the plunger 400 and up into the upper portion between the rod seal 404 and the plunger stopper 406. Between the rod seal 404 and the plunger stopper 406, there is an optional storage chamber 420 for air or for a desiccant to keep lyophilized reagent dry, for example.

FIG. 10B shows plunger 400 in a start position. FIG. 10C shows (with arrow) the plunger rod 402 being pushed downward. The reconstitution buffer may be an incompressible liquid that then pushes on the bypass stopper 410 when compressed by the rod seal 404. Therefore, as the plunger rod 402 is depressed downward, the rod seal applies pressure on the reconstitution buffer 408, which similarly applies pressure on the bypass stopper 401. As pressure is applied to the bypass stopper 410, the bypass stopper 410 moves down a length of the plunger 400 toward the bypass feature 412. Air is drawn back to the storage chamber 420 from the bottom of the plunger 400 and through air exchange channel 418, though some air will still exit the outlet opening 416. In some examples, a vent may be located downstream during the plunging operation, such as the vent located at seal 530 in FIG. 12. Such vent may allow for the integration of a backpressure bubble valve for system 450 in FIG. 12 and having a location for desiccant (illustrated as 426 in FIG. 12A). FIG. 10D shows that when the bypass stopper 410 reaches the bypass feature 412, liquid (in this example, reconstitution buffer) is allowed to bypass the stopper 410 and reach the lyophilized reagent 414. FIG. 10E shows that with continued displacement of the plunger rod 402, the liquid reconstitution buffer 408 will be forced into the lower chamber 422 with the dry lyophilized reagent 414 and will wet the lyophilized reagent 414.

An example bypass feature 412 is an opening in the inner cylinder wall 424 of the plunger 400, which will allow fluid to flow around the elastomer seal of the bypass stopper 410 as it is pushed downward close to the bypass feature 412. Another example bypass feature 412 is a rib on the inner cylinder wall 424 of the plunger 400 that may locally lift the seal of the bypass stopper 410, as it is pushed downward adjacent to the bypass feature 412, to allow fluid to flow through an opening into the lower chamber 422. Other example bypass features are also contemplated.

FIGS. 11A-C show an example plunger 450 for adding lysing/binding buffer to a sample and how the plunger 450 may function in a PCR system, such as the system 350 of FIG. 9, for example. FIG. 11A labels the components of the plunger 450 and reagents or fluids, for example, that may be in the plunger 450. Starting at the top of plunger 450, a plunger rod 452 extends from outside the top of the plunger 450, through a rod seal 454, which seals contents of the plunger 450 to inside the plunger 450. The bottom end, being inside the plunger 450, of the plunger rod 452 contains a plunger stopper 456, which may push on some reagent or other fluids in the plunger 450. The plunger stopper 456 may have a suitable diameter that allows the plunger stopper 456 to fit and yet slide against the inner cylinder wall 476 of the plunger 450.

Between plunger stopper 456 and a bypass stopper 460, which also fits against the inside wall of the plunger 450, may be a lysing/binding buffer 408. Below the bypass stopper 460 may be a bypass feature 462. An empty lower chamber 464 may be located below the bypass feature 462. An output channel 466 may be located near the bottom of plunger 450, which is connected to a sample input chamber 468. As shown, a sample swab 470 may be loaded into the sample input chamber 468. An air exchange channel 472 may extend between the top of the sample input chamber 468 and the upper chamber 474 of the plunger 450.

FIG. 11A shows a start position of plunger 450. FIG. 11B shows (with arrow) the plunger rod 452 being pushed downward. The lysing/binding buffer is an incompressible liquid that then pushes on the bypass stopper 460. Air is pushed out of the lower chamber 464 through outlet channel 466 into the sample input chamber 468. FIG. 11C shows that when the bypass stopper 460 reaches the bypass feature 462, liquid is allowed to bypass the stopper 460 and reach the lower chamber 464 and move out through the outlet channel 466 into sample input chamber 468. The sample swab 470 may be immersed in the lysing/binding buffer. The buffer with sample dissolved or suspended in the buffer then is pushed out a final output channel 478 and to a microfluidic reaction chamber.

An example bypass feature 462 may be an opening in the inner cylinder wall 476 of the plunger 450, which will allow fluid to flow around the elastomer seal of the bypass stopper 460 as it is pushed downward close to the bypass feature 462. Another example bypass feature 462 is a rib on the inner cylinder wall 476 of the plunger 450 that may locally lift the seal of the bypass stopper 460 as it is pushed downward adjacent to the bypass feature 462, to allow buffer to flow through an opening into the lower chamber 464.

Figure 12A:
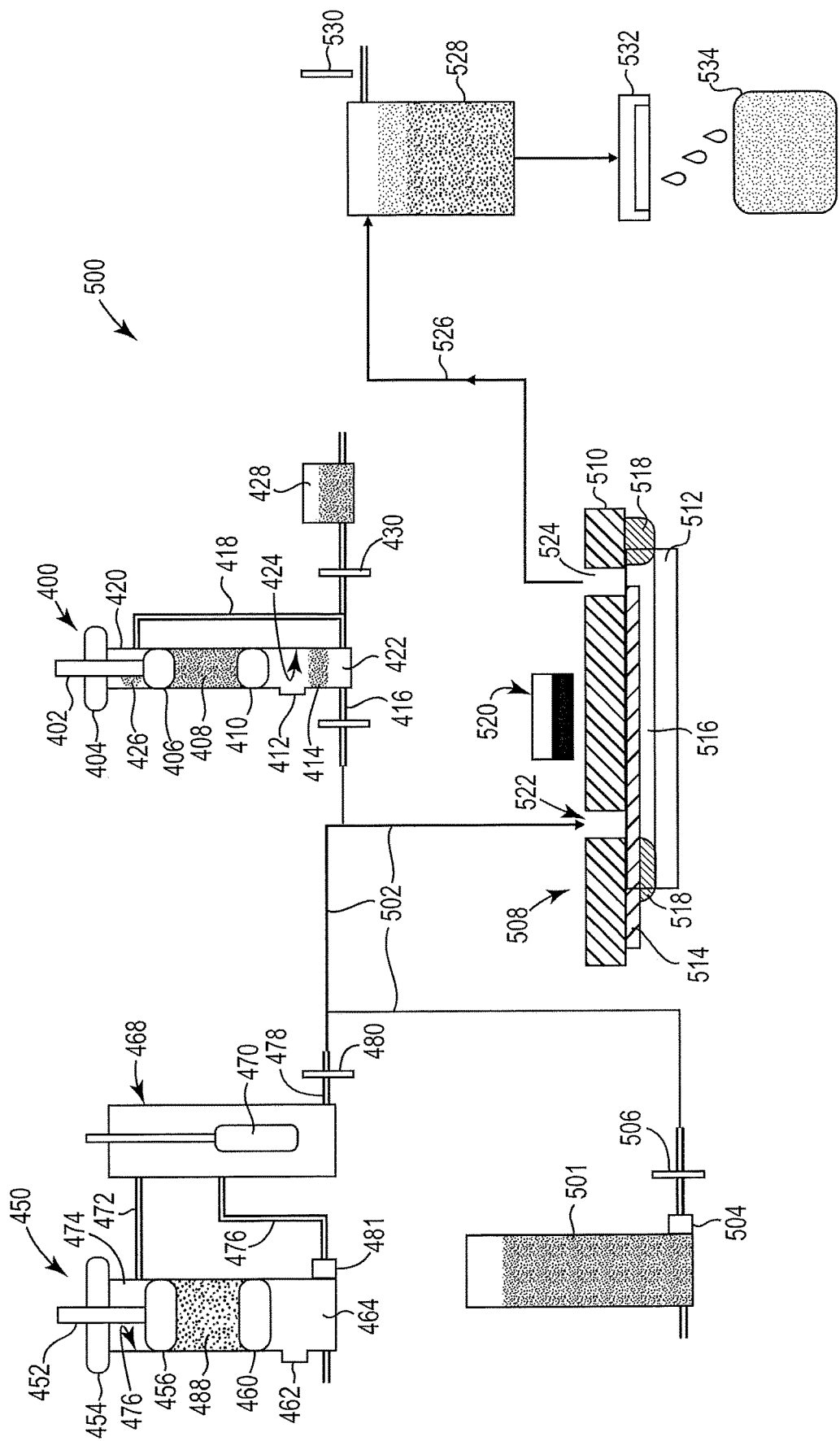
FIG. 12A-12B are schematic diagrams of an example PCR system including a microfluidic reaction chamber, according to the present disclosure.

FIG. 12A shows an example PCR system 500, which includes both a plunger for reconstitution of lyophilized reagent (plunger 400 in FIGS. 10A-E) and a plunger for adding lysing/binding buffer to a sample (plunger 450 in FIGS. 11A-C). The description above of both plungers 400, 450 applies to the system 500 and will not be repeated with regards to FIG. 12A.

System 500 includes plunger 450 to introduce a sample to the microfluidic reaction chamber 508. The example plunger 450 in FIG. 12A, however, includes an additional component, which is a filter flow stop 480 between the plunger 450 and the sample input chamber 468. The example plunger 400, to reconstitute lyophilized reagent, also includes an additional component in FIG. 12A. A backpressure bubbler 428 is connected to plunger 400. The plungers 400 and 450, and a wash buffer chamber 501 may be connected to a microfluidic reaction chamber 508 by a plurality of capillaries 502. Isolation seals 430, 480, 506 may be located between both the plungers 400, 450 and the wash buffer chamber 501, and the microfluidic reaction chamber 508.

The example microfluidic reaction chamber 508 shown includes a substrate 510 with an input opening 522 through which to receive the fluids from both plungers 400, 450 and the wash buffer chamber 502. The description of corresponding components of other example microfluidic reaction chambers described herein apply to the microfluidic reaction chamber 508 of FIG. 12A. The microfluidic reaction chamber 508 includes a lid 512 mounted to a substrate using adhesive portions 518. A reaction-chamber circuit 514 is included, and a via 516 is formed between lid 512 and reaction-chamber circuit 514. PCR takes place in the microfluidic reaction chamber 508. A trapping region (not visible) may be included in the microfluidic reaction chamber 508. A magnet 520 may also be located adjacent the trapping region. Waste fluids may move through output opening 524 and run through a capillary 526 to a waste storage and drive fluid chamber 528. The waste and drive fluid may flow through a thermal inkjet drop ejector 532 and may be ejected into an absorber 534.

Figure 12B:
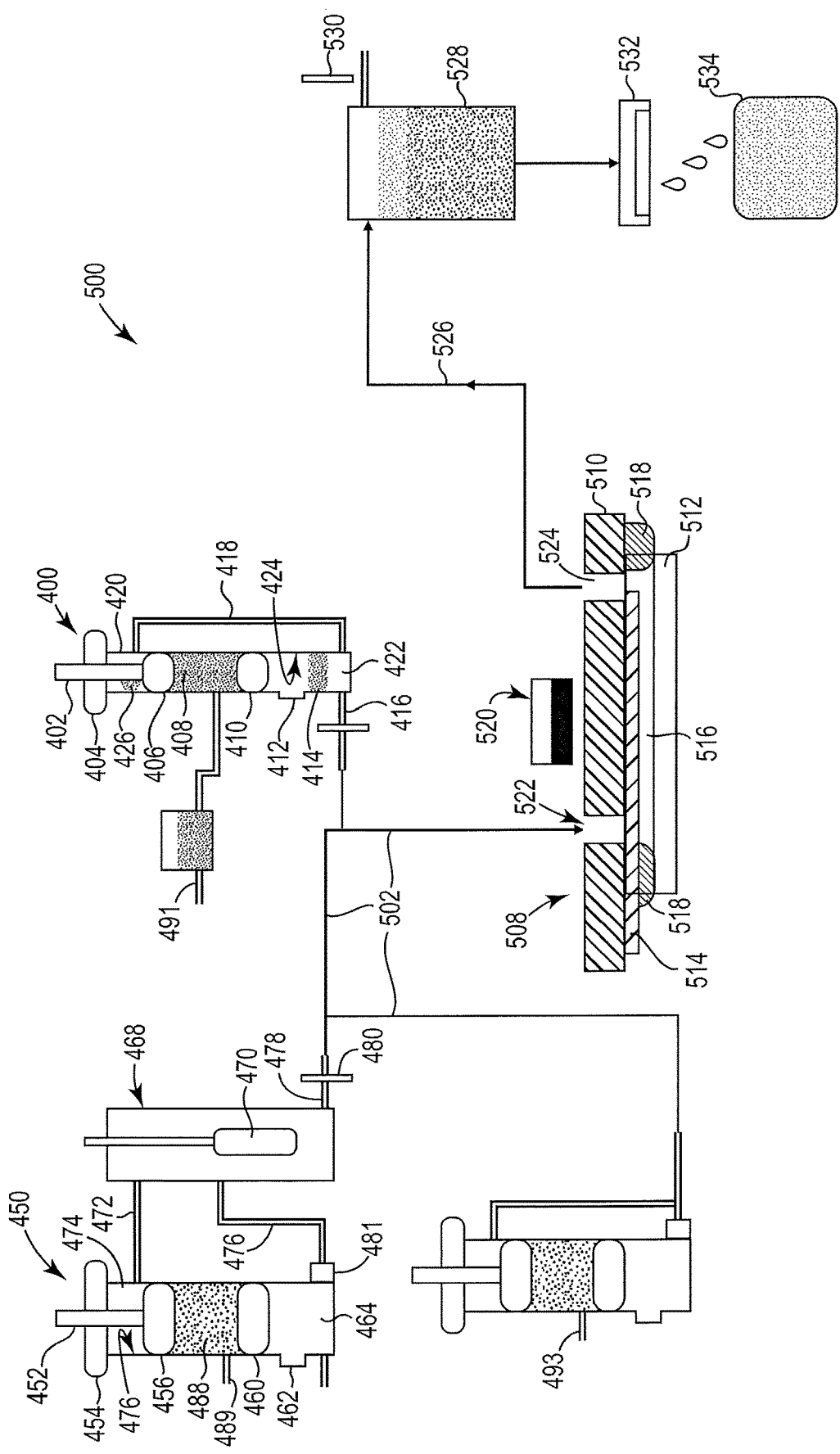

FIG. 12B shows an additional example of PCR system 500, which includes a plunger for reconstitution of lyophilized reagent (plunger 400 in FIGS. 10A-E), a plunger for adding lysing/binding buffer to a sample (plunger 450 in FIGS. 11A-C), and a plunger for the wash buffer 501. The description above of both plungers 400, 450 applies to the system 500 and will not be repeated with regards to FIG. 12B. Additional components that may be added to system 500 include a backpressure bubbler 489 that may be added to plunger 450, and a backpressure bubbler 493 for the wash buffer chamber 501. Additionally, the backpressure bubbler 491 connected to plunger 400 may be modified, and located mid-way down the plunger 400 rather than at the bottom of the plunger 400 (as illustrated). In various examples, the backpressure bubblers may operate in an ordered sequence. For instance, backpressure bubbler 489 may first operate in the sequence, then backpressure bubbler 493 may operate, and third the backpressure bubbler 491 may operate.

Figure 13:
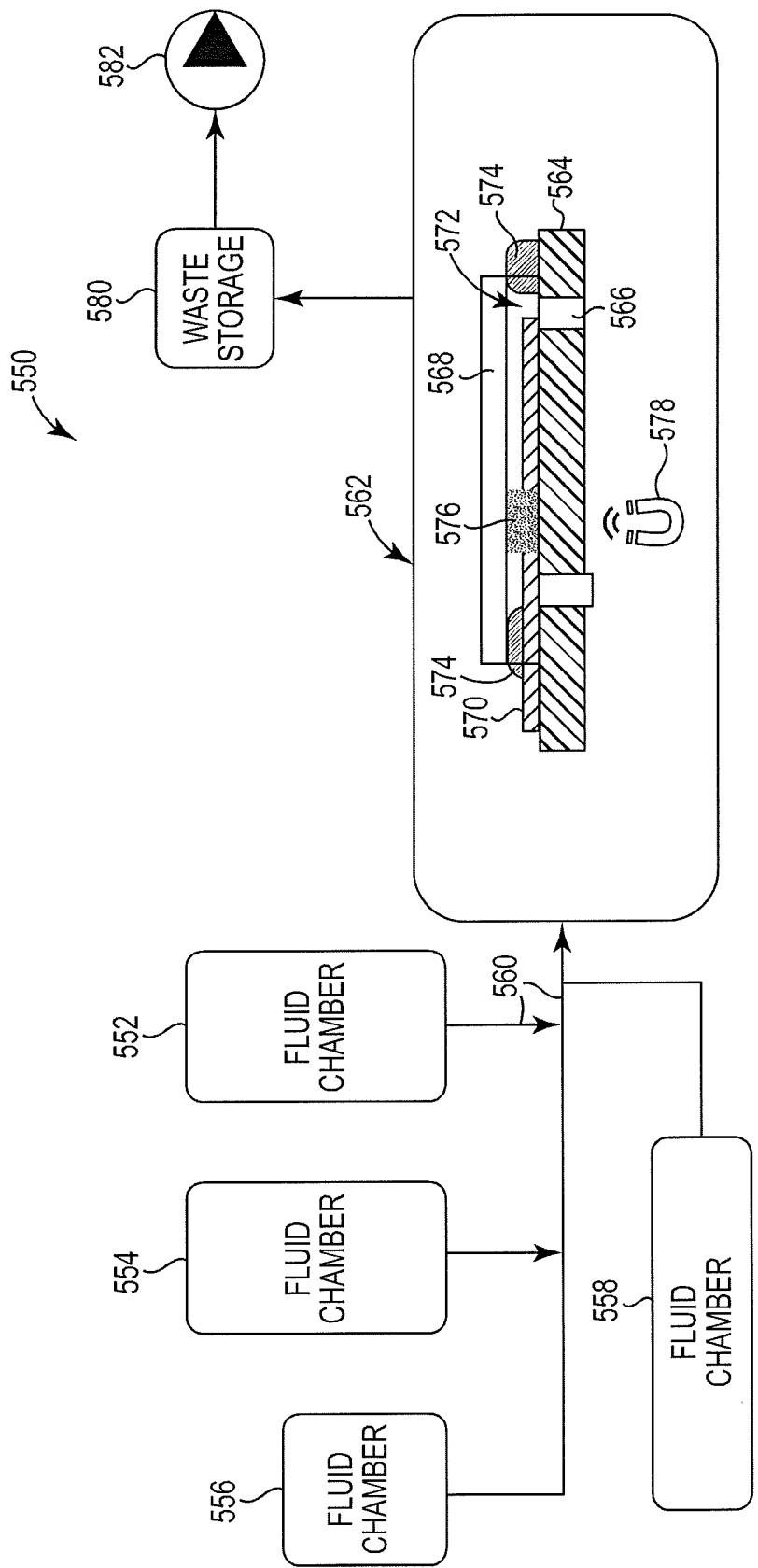
FIG. 13 is a schematic diagram of an example PCR system including a microfluidic reaction chamber, according to the present disclosure.

FIG. 13 shows a schematic view of an example two-step reverse transcription PCR system 550 for detecting RNA. The description of the parts or components of systems above apply to corresponding parts in system 550. In system 550, four fluid chambers 552, 554, 556, 558 are shown, but other numbers of fluid chambers are contemplated. A first fluid chamber 552 may include a dry master mix and a reconstitution buffer. A second fluid chamber 554 may include a sample, a lysing/binding buffer and paramagnetic beads. A third fluid chamber 556 may include a wash buffer. A fourth fluid chamber 558 may include a supply of a dry Master mix with chemistry suitable for reverse transcription, and a reconstitution buffer, where the fourth fluid chamber 558 is separated from the other fluid inputs used for PCR. The fluid inputs within the fluid chambers 552, 554, 556, 558 may be driven or moved through a plurality of capillaries 560 that extend between the fluid chambers 552, 554, 556, 558 and a microfluidic reaction chamber 562. The fluid inputs may also be driven by a pump 582 that is downstream in the system 550. The remainder of the system 550, including the microfluidic reaction chamber 562, may include similar components to those in other systems described herein. The microfluidic reaction chamber 562 includes a lid 568 attached or mounted to a substrate 564, with a reaction-chamber circuit 570 mounted to the substrate 564. The lid 568 and reaction-chamber circuit 570 form a via 572 there between through which fluid inputs may be driven. A trapping region 576 is located within the microfluidic reaction chamber 562, and a magnet is shown 578. A waste storage chamber 580 is located downstream from the microfluidic reaction circuit 562.

In the method illustrated in FIG. 13, after the lysed sample is expelled from fluid chamber 554, the fourth fluid input may be pulled into the microfluidic reaction chamber 562 (e.g., from the fourth fluid chamber 558) first and incubated in the microfluidic reaction chamber 562 to create complementary DNA (cDNA) from the lysed sample. As the reconstituted master mix with chemistry suitable for reverse transcription is purged from the microfluidic reaction chamber 562 to a waste storage chamber 580, the second master mix reconstitution from the first fluid chamber 552 is pulled into the microfluidic reaction chamber 562. The cDNA in the microfluidic reaction chamber 562 then undergoes PCR.

Another example method for reverse transcription PCR for detecting RNA is a one-step method. The one-step method may utilize, for example, system 50 of FIG. 2, and will be described with regards to that figure. In the example method, paramagnetic beads may be added to the lysis/binding buffer that is added to the sample in fluid chamber 52 prior to introduction of the sample to the microfluidic reaction chamber 58. The paramagnetic bead surface chemistry may be designed to capture RNA. The master mix in fluid chamber 54 may include reverse transcriptase to convert RNA into cDNA during an additional heating step in the microfluidic reaction chamber 58. The step of converting RNA into cDNA may be carried out prior to PCR to amplify and detect cDNA.

The example systems descried herein may process both RNA and DNA targets using different biochemistries. The example systems may accommodate biochemistries that utilize multiple cycling between temperatures (e.g., thermocycling), such as reverse transcription PCR (RT-PCR), PCR, and quantitative PCR (qPCR), for example. The example systems may also be compatible with isothermal biochemistries, such as loop-mediated isothermal amplification (LAMP), recombinase polymerase amplification (RPA), helicase dependent amplification (HDA), and nicking enzyme amplification reaction (NEAR), for example.

Figure 14B:
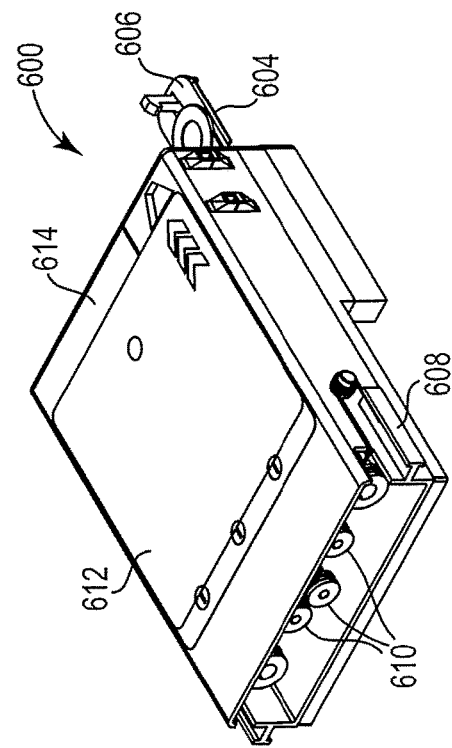
FIGS. 14A-14D illustrate perspective views of an example cartridge as may be implemented in the PCR system of the present disclosure.
Figure 14D:
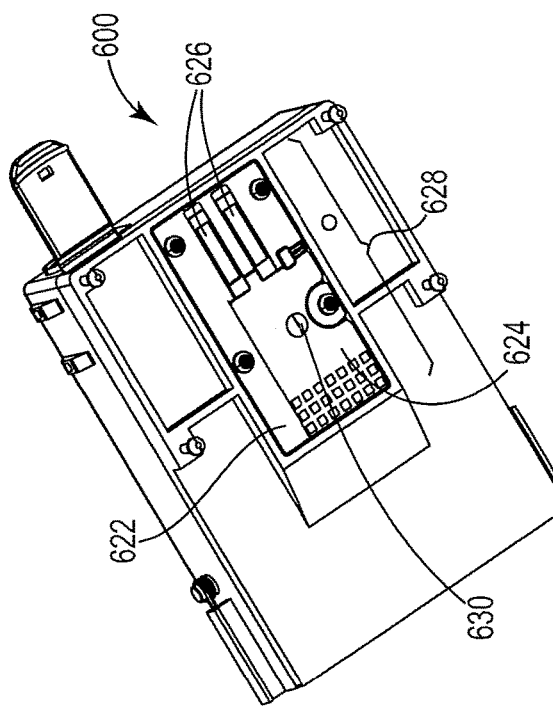
Figure 14A:
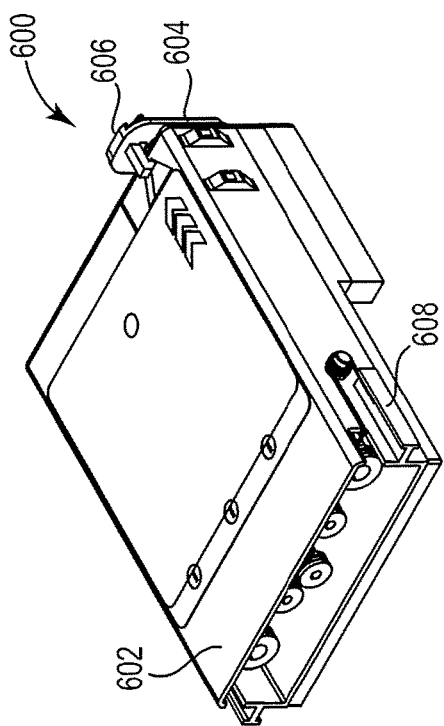

FIG. 14A shows a perspective view from the top of an example cartridge 600 in which microfluidic PCR may be performed. The components of any of the systems described herein may be housed in the cartridge 600, for example, and any method of PCR described herein may be performed in cartridge 600. Visible in FIG. 14A is a housing or body 602 of the cartridge 600. Also, a sample input port 604, having a port cover 606, is in a closed position. A plunger locking bar 608 is also visible in the figure. Although not indicated on the figure, there may be a single or multiple fill ports in the body 602.

FIG. 14B shows a first perspective, cut-away view from the top of the cartridge 600 in FIG. 14A. The sample input port 604 is in an open position, being ready to accept a sample or sample swab. The plunger locking bar 608 is visible. Also, plunger 610 is shown. There is a plunger reagent storage system 612, and a thermal inkjet driving fluid storage 614.

Figure 14C:
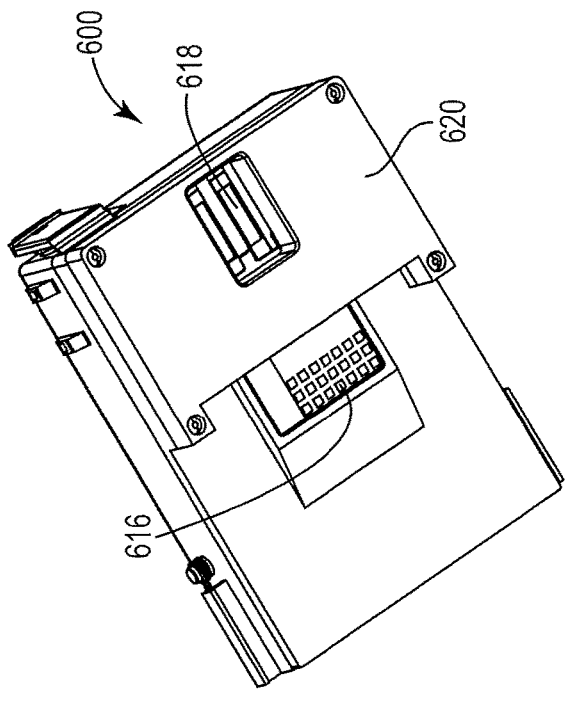

FIG. 14C shows a perspective, bottom view of the cartridge 600. The cartridge may include an electrical interconnect 616, as shown. Also, cartridge 600 includes an optical access 618 to a PCR reaction chamber inside, and an absorber housing 620.

FIG. 14D shows a perspective, cut-away, bottom view of cartridge 600. As shown, cartridge 600 may include an electronics package 622, and a printed circuit board (PCB) 624. Additionally, there may be microfluidic reaction chambers 626, as described herein. Collectively, the electronics package 622, the PCB 624, and the microfluidic chambers 626 may comprise a thermal inkjet printhead 628. In various examples, the thermal inkjet printhead 628 may include a security chip 630, which may be under an encapsulate.

FIG. 15A shows an exploded view of an example thermal inkjet printhead 643, illustrated as 628 from cartridge 600 in FIG. 14D. Starting from the bottom of the figure, a magnet 632 is shown, which may or may not utilize a shield (not shown). Above the magnet 632 is a substrate 634 that may include a plurality of openings 636 there through, which may serve as input/output openings, for example. Above the substrate 634 may be a film adhesive 638, as shown. The film adhesive 638 may be a pressure-sensitive adhesive (PSA), for example. Above the film adhesive 638, may be a PCB 624. The PCB 624 may include silicon chips 642 for thermal cycling and sensing. A security chip 630 may be included. A plurality of lids 646 may be included. Adhesive portions 648 are shown that may be included to mount the PCB 624 on the substrate 634, for example.

FIG. 15B shows an exploded view of cartridge 600 of FIGS. 14A-D. Starting near the bottom is an overmolded manifold 652, which houses the components of FIG. 15A. A chip package 603 may be attached below the manifold 652, and may be attached with screws or swage posts 656, for example. A shroud 658 may be included that may include an absorber for ejected drive fluid, for example. The shroud 658 may be attached to the manifold 652 using swage posts 660, for example. The sample input port cover 606 may be located on the manifold 652. The body 602 of the cartridge 600 may be above the manifold 652. Housed in the body 602 are a plurality of plungers 610 with stoppers, as discussed herein. Also shown are a plurality of seals 662 that extend around an outer end of each plunger. Shown are two one-time valves 664 (or stoppers), and two bubbler stop filters 666. A torsion spring 668 may also be included in the body 602 to retain the plungers 610.

Above the body 602 is shown a filter 670, and then a foam 672 for drive fluid. A waste absorber 674 is shown above the foam 672, and a lid 676 is shown above the waste absorber 674. A plurality of ball bubblers 678 (three are shown) may be included. A label 680 may be the top-most component, as shown in FIG. 15B.

Figure 16:
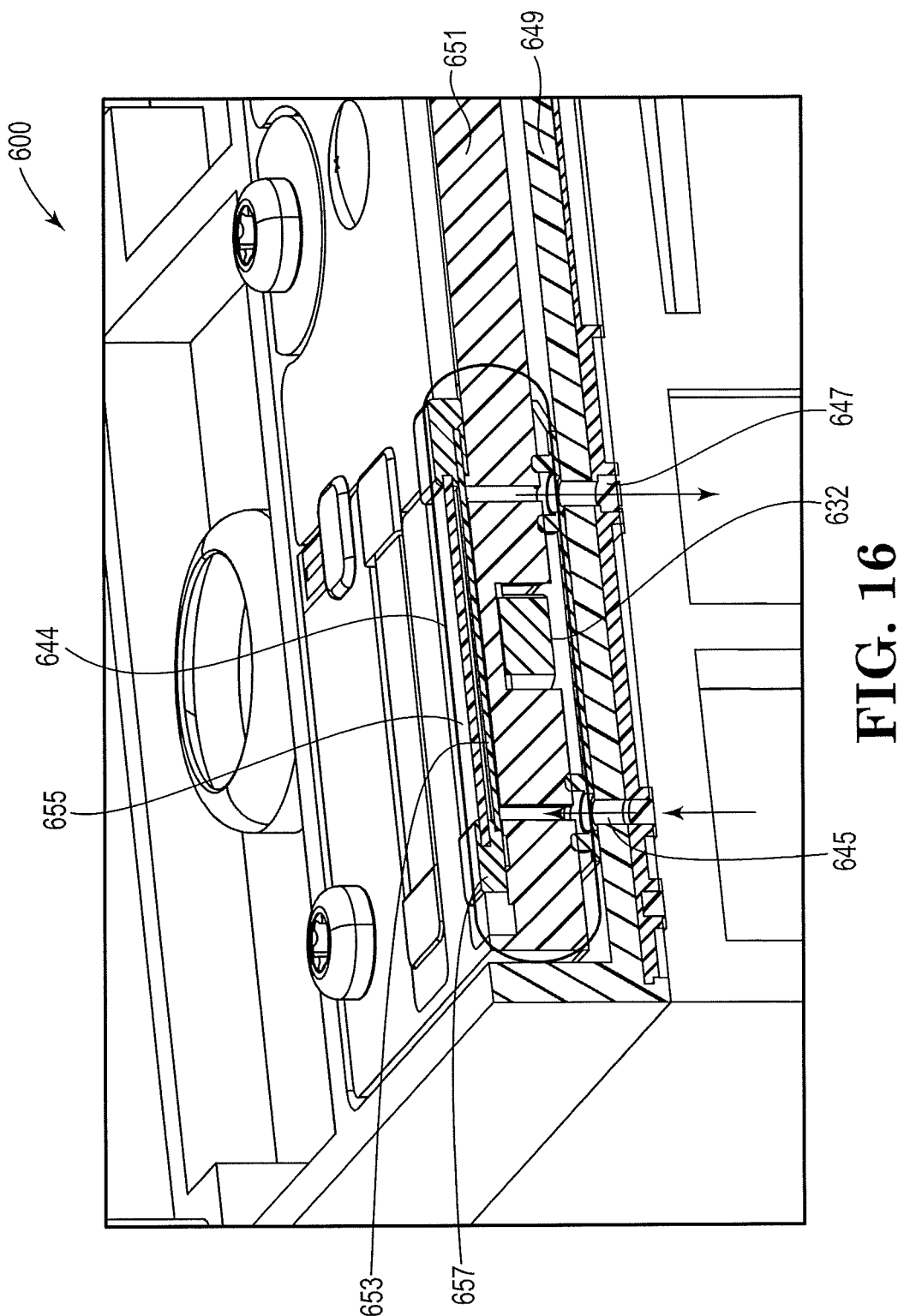
FIG. 16 is a close-up view of a portion of the cartridge of FIG. 14A, according to the present disclosure.

FIG. 16 is a close-up view of a portion of cartridge 600. The microfluidic reaction chamber 644 is shown, which may be about 2.5 microliters and 19 mm long, for example, although other sizes or measurements are contemplated. The permanent magnet 632 is shown, which may include a metal shield (not shown). In the example illustrated in FIG. 16, fluid from the fluid chambers may enter the microfluidic reaction chamber 644 through input opening 645 (e.g., a hole defined by walls of the manifold 649 and the substrate 651), and exit the microfluidic reaction chamber 644 through an output opening 647 (e.g., a hole defined by walls of the manifold 649 and the substrate 651). A microfluidic reaction circuit 653 may heat the fluid passing from the fluid input opening 645 to the fluid output opening 647, and beneath a lid 655. As discussed elsewhere herein, the fluid may pass through a via created between the microfluidic reaction circuit 653 and the lid 655. Adhesive or other anchoring apparatus 657 may secure the lid 655 to the substrate 651, as discussed herein.

Figure 17A:
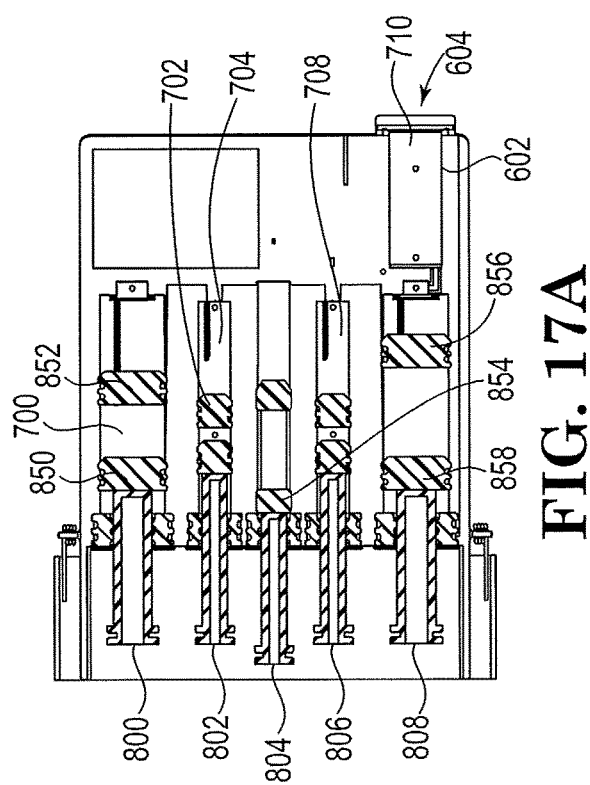
FIGS. 17A-17E illustrate cut-away views of a portion of the cartridge of FIG. 14A, according to the present disclosure.

FIGS. 17A-E show cut-away views of the body 602 portion of cartridge 600 with plungers (five are shown) in channels, or reagent chambers, which may be actuated in an example plunger sequence. The plungers (800, 802, 804, 806, and 808) may be used in an example PCR reaction performed by cartridge 600. FIG. 17A is an example starting position of the cartridge 600 in an example PCR reaction. Starting at the top of FIG. 17A, a first fluid chamber 700 is shown, which may include wash buffer, for example. A first plunger 800, of the plurality, is shown slidably received in a first channel 850 with the first fluid chamber 700. A second plunger 802 is slidably received in a second channel 852. Also in the second channel 852 is a second fluid chamber 702, which may include a reconstitution buffer to be mixed with and a first lyophilized master mix 704, for example. A third channel 854 is shown that may slidably receive a third plunger 804. The third channel 854 may be a vent, for example. A fourth channel 856 is shown that may slidably receive a fourth plunger 806. Also, in the fourth channel 856 may be a third fluid chamber 708 that may include a reconstitution buffer and a second lyophilized master mix, for example. A fifth channel 858 may slidably receive a fifth plunger 808. Also in the fifth channel 858, may be a fifth fluid chamber 710 that may include a lysing/binding buffer. The fifth channel 858 may also receive a sample or a sample swab through sample input port 604.

Figure 17B:
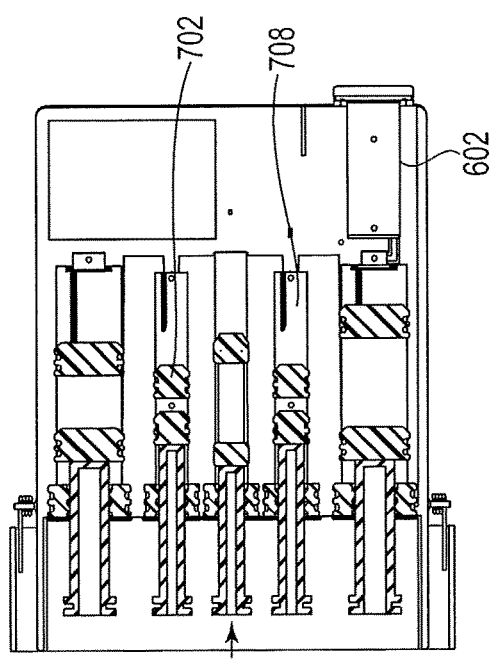
Figure 17C:
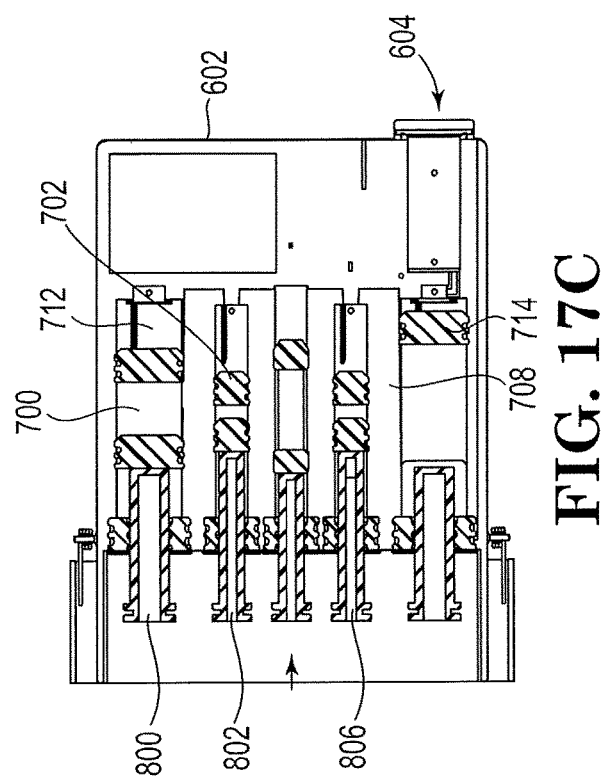

FIG. 17B shows the next step in the example plunger sequence, which may be the second of five steps in the example sequence. As shown, second fluid chamber 702 and fourth fluid chamber 708, that may contain lyophilized master mix, may be unsealed. FIG. 17C shows a third step, which may include pushing (with first plunger 800) wash buffer from the first fluid chamber 700 into a first seal defeat feature 712, which may compromise a wash buffer seal. Also, the reconstitution buffers in both second fluid chamber 702 and fourth fluid chamber 708 may be pushed along by second and fourth plungers (802, 806, respectively) along in the second and fourth channels (852, 856, respectively). Also, a binding buffer seal may be pushed into a second seal defeat feature 714 in fifth channel 858 by fifth plunger 808.

Figure 17E:
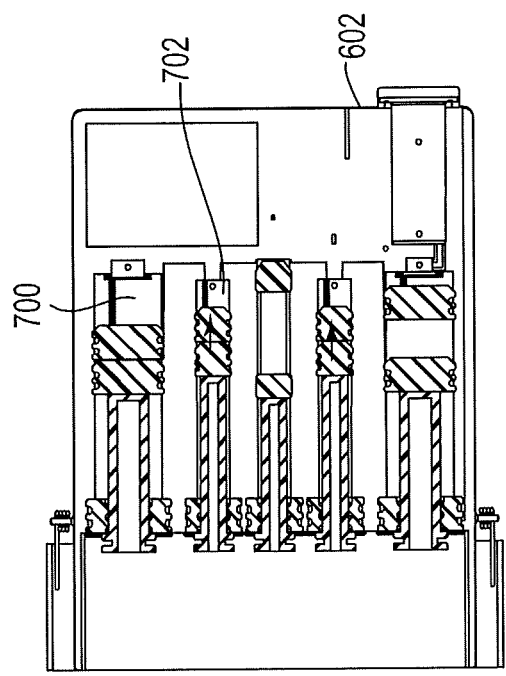
Figure 17D:
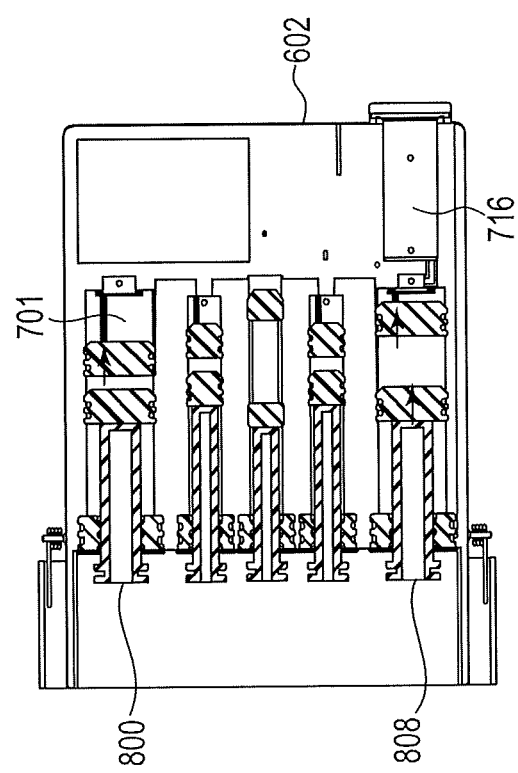

FIG. 17D shows a fourth step in the sequence. Seals for second and fourth fluid chambers (702, 708, respectively) housing reconstitution buffer are compromised. Wash buffer in the first channel 805 is pushed by plunger 800 into a second chamber 701 that may be part of fluid chamber 700. Binding buffer in the fifth channel 858 may be pushed by plunger 808 past a seal and ultimately into the sample input chamber 716.

FIG. 17E shows a final plunger position in a sequence for use in an example PCR reaction. Wash buffer from first fluid chamber 700 may be loaded into the microfluidic reaction chamber (not shown). In second fluid chamber 702, reconstitution buffer may be pushed into lyophilized master mix. The vent in third channel 854, may store drive fluid, and excess air during plunger actuation. The vent may be sealed. In fourth fluid chamber 706, reconstitution buffer may be pushed into lyophilized master mix. In the sample input chamber 716, lysing/binding buffer may be mixed with the sample.

FIGS. 18A-D show perspective views of example steps in a method of loading a sample into the cartridge 600. In FIG. 18A, sample port cover 606 is shown in an open position exposing sample input port 604. A sample swab 900 that may include a sample portion 902 and a handle portion 904 is shown in close proximity to cartridge 600. In FIG. 18B, sample portion 902 is inserted into sample input port 604. In FIG. 18C, the handle portion 904 of sample swab 900 is shown being moved upwardly in order to break the handle portion 904 off from the sample portion 902, which is inside cartridge 600. FIG. 18D shows sample port cover 606 closed, which encloses sample portion 902 of sample swab 900 into sample input chamber 716 of cartridge 600. Closing the sample port cover 606 may begin a process such as that described with regards to FIGS. 17A-E.

An example method of PCR, such as that shown in FIGS. 12A-12B3 that may use the cartridge 600 as shown in preceding figures, will be described. A sample may be placed in sample input chamber 716 (FIG. 18D), which is closed or self-sealed. The sample port cover 606 may be closed. Internal sealing valves may be either opened or closed when the sample port cover 606 is closed. Parallel plungers in the cartridge 600 (800, 802, 808) may then be actuated to force lysis/binding buffer into the sample input chamber 716, and to force reconstitution buffer to mix with lyophilized Master mix, and to load wash buffer into the fluid network. The valves and plungers may be actuated in parallel or sequentially. The plunger and internal valves may be actuated by sealing of the sample input chamber 716 by a user, by latching the cartridge 600 into another instrument (such as a receiving apparatus) by a user, by mechanical actuators in the instrument, or by motorized load of the cartridge 600 into an instrument, for example. An example of a mechanical actuator may include receiving an actuation signal from an actuation circuit in the nucleic acid amplification cartridge. The plungers, like those shown in FIGS. 10A-E and 11A-C, may translate the stored liquid 408 and the elastomeric stopper 410, 460 between wet and dry volumes until a feature such as a groove or protrusion in the plunger inner wall or a bypass path defeats the seal and allows the liquid to bypass the elastomeric seal.

Chemical lysing of the cells in the sample may be performed, and the extracted nucleic acids may be bound to paramagnetic beads. In parallel, the master mix may be reconstituted. Alternatively, lysing may be performed with heat or mechanically such as by ultrasonic displacement of the sample, for example. A downstream pump may then pull the lysed sample through the microfluidic reaction chamber. Paramagnetic beads with bound nucleic acids may then be trapped by a magnetic field. The rest of the components may then continue to the waste chamber. The downstream pump may then pull wash buffer through the microfluidic reaction chamber to purge it of components that may interfere with nucleic acid amplification reaction or nucleic acid detection. Next, the pump may pull reconstituted master mix (which contains the chemical components for nucleic acid amplification and detection) into the microfluidic reaction chamber. A sensor on the reaction-chamber circuit may detect when the chamber is filled with master mix and it may signal the downstream pump to stop. Next, the nucleic acids may be amplified using PCR by thermal cycling the fluid. PCR may be completed in less than five minutes due to the small microfluidic volumes, chemical component concentration, and efficiency of thermal heating from a silicon chip. Reporter molecules for target nucleic acids may be sensed optically or electrochemically by sensors on the reaction-chamber circuit in real time or near real time. Alternatively, the reporter molecules may be sensed optically off-board through a glass lid, for example.

In some examples, the microfluidic device may include inertial pumps to actively move fluids through the microfluidic channels. An inertial pump may include a fluid actuator such as a piezoelectric element or a thermal resistor. The fluid actuator may displace fluid by moving a piezoelectric element or boiling the fluid to form a vapor bubble.

The term "sample," as used herein, generally refers to any biological material, either naturally occurring or scientifically engineered, which contains at least one nucleic acid which may also include other non-nucleic acid material, such as biomolecules (e.g., proteins, polysaccharides, lipids, low molecular weight enzyme inhibitors, oligonucleotides, primers, templates), polyacrylamide, trace metals, organic solvents, etc. Examples of naturally-occurring samples or mixtures include, but are not limited to, whole blood, blood plasma, and other body fluids, as well as tissue cell cultures obtained from humans, plants, or animals. Examples of scientifically-engineered samples or mixtures include, but are not limited to, lysates, nucleic acid samples eluted from agarose and/or polyacrylamide gels, solutions containing multiple species of nucleic acid molecules resulting either from nucleic acid amplification methods, such as PCR amplification or reverse transcription polymerase chain reaction (RT-PCR) amplification, or from RNA or DNA size selection procedures, and solutions resulting from post-sequencing reactions. However, the sample will generally be a biological sample, which may contain any viral or cellular material, including all prokaryotic or eukaryotic cells, viruses, bacteriophages, mycoplasmas, protoplasts, and organelles. Such biological material may thus comprise all types of mammalian and non-mammalian animal cells, plant cells, algae including blue-green algae, fungi, bacteria, protozoa, etc. Representative samples thus include whole blood and blood-derived products such as plasma, serum and buffy coat, urine, feces, cerebrospinal fluid or any other body fluids, tissues, cell cultures, cell suspensions, etc. The sample may comprise a lysate. The sample may also include relatively pure starting material such as a PCR product, or semi-pure preparations obtained by other nucleic acid recovery processes.

In the present specification and in the appended claims, the term "fluid" is meant to be understood broadly as any substance that continually deforms (flows) under an applied shear stress. In one example, a fluid includes an analyte. In another example, a fluid includes a reagent or reactant. In another example, a fluid includes an analyte and a reagent or reactant. In still another example, a fluid includes an analyte, a reagent or reactant, among others. Additionally, in the present specification and in the appended claims the term "analyte" is meant to be understood as any substance within a fluid that may be placed in a microfluidic diagnostic chip (MDC). In one example, the analyte may be any constituent substance within a fluid such as, but not limited to, animal or human blood, animal or human urine, animal or human feces, animal or human mucus, animal or human saliva, yeast, or antigens, among others. Further, as used in the present specification and in the appended claims, the term "pathogen" is meant to be understood as any substance that can produce a disease. In one example, the pathogen may be found in any fluid as described above. Still further, in the present specification and in the appended claims the term "reagent" is meant to be understood as a substance or compound that is added to a system in order to bring about a chemical reaction, or added to see if a reaction occurs. A reactant is meant to be understood as a substance that is consumed in the course of a chemical reaction.

Terms to exemplify orientation, such as upper/lower, left/right, top/bottom and above/below, may be used herein to refer to relative positions of elements as shown in the figures. It should be understood that the terminology is used for notational convenience only and that in actual use the disclosed structures may be oriented different from the orientation shown in the figures. Thus, the terms should not be construed in a limiting manner.

The skilled artisan would recognize that various terminology as used in the Specification (including claims) connote a plain meaning in the art unless otherwise indicated. The terms "comprise(s)," "include(s)," "having," "has," "can," "may," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other examples "comprising," "consisting of" and "consisting essentially of," the examples or elements presented herein, whether explicitly set forth or not.

As additional examples, the specification describes and/or illustrates aspects useful for implementing the claimed disclosure by way of various structure, such as circuits or circuitry selected or designed to carry out specific acts or functions, as may be recognized in the figures or the related discussion as depicted by or using terms such as blocks, modules, device, system, unit, controller, and/or other examples. It will also be appreciated that certain of these blocks may also be used in combination to illustrate examples of how operational aspects (e.g., steps, functions, activities, etc.) have been designed, arranged. Whether alone or in combination with other such blocks (or circuitry including discrete circuit elements such as transistors, resistors etc.), these above-characterized blocks may be circuits configured/coded by fixed design and/or by (re)configurable circuitry (e.g., CPUs/logic arrays/controllers) and/or circuit elements to this end of the corresponding structure carrying out such operational aspects. In certain examples, such a programmable circuit refers to or includes one or more computer circuits, including memory circuitry for storing and accessing a set of program code to be accessed/executed as instructions and/or (re)configuration data to perform the related operation, as may be needed in the form of carrying out a single step or a more complex multi-step algorithm. Depending on the data-processing application, such instructions (and/or configuration data) may be configured for implementation in logic circuitry, with the instructions (via fixed circuitry, limited group of configuration code, or instructions characterized by way of object code, firmware and/or software) as may be stored in and accessible from a memory (circuit).

As another example, where the specification may make reference to a "first [type of structure]", a "second [type of structure]", etc., where the [type of structure] might be replaced with terms such as circuit, circuitry, and others, the adjectives "first" and "second" are not used to connote any description of the structure or to provide any substantive meaning; rather, such adjectives are merely used for English-language antecedence to differentiate one such similarly-named structure from another similarly-named structure designed or coded to perform or carry out the operation associated with the structure (e.g., "first circuit to convert . . . " is interpreted as "circuit to convert . . . ").

Based upon the above discussion and illustrations, those skilled in the art will readily recognize that various modifications and changes may be made to the various examples without strictly following the exemplary examples and applications illustrated and described herein. For example, methods as exemplified in the Figures may involve steps carried out in various orders, with one or more aspects of the examples herein retained, or may involve fewer or more steps. For instance, more or fewer steps beyond those described with regards to FIGS. 17 and 18 may be performed. Such modifications do not depart from the true spirit and scope of various aspects of the disclosure, including aspects set forth in the

What is claimed is:

1. An apparatus comprising:
   a microfluidic reaction chamber including a reaction-chamber circuit to process a reagent and a biologic sample for amplification of nucleic acids included in the biologic sample;
   a plurality of capillaries to pass the reagent and the biologic sample through the microfluidic reaction chamber;
   each of a plurality of valves respectively disposed in different ones of the plurality of capillaries;

a valve control system to selectively control each of the plurality of valves and, during operation, to cause the reagent and the biologic sample to selectively move through the microfluidic reaction chamber according to a particular timing sequence; and a trapping region disposed in the microfluidic reaction chamber to secure the nucleic acids in the microfluidic reaction chamber for the amplification of the nucleic acids using the reaction-chamber circuit; and a pump disposed on a side of the microfluidic reaction chamber, wherein the pump is to terminate a flow of a reconstituted reagent solution from a second fluid chamber to the microfluidic reaction chamber when a level of the reconstituted reagent solution in the microfluidic reaction chamber reaches a threshold level.

2. The apparatus of claim 1, further including:

a first fluid chamber coupled to the plurality of capillaries, the first fluid chamber having a first plunger to, responsive to receipt of the biologic sample, mix the biologic sample with a lysis solution; and the second fluid chamber coupled to the plurality of capillaries, the second fluid chamber including a lyophilized reagent solution and a second plunger to allow a buffer to mix with the lyophilized reagent solution when depressed beyond a threshold within the second fluid chamber and form the reconstituted reagent solution;

wherein the valve control system is to selectively move the biologic sample with the lysis solution, and the reconstituted reagent solution, through the microfluidic reaction chamber according to the particular timing sequence.

3. The apparatus of claim 2, wherein the pump is disposed on a different side of the microfluidic reaction chamber relative to a side of the microfluidic reaction chamber on which the first and second fluid chambers are disposed.

4. The apparatus of claim 1, further including:

a first fluid chamber coupled to the plurality of capillaries, the first fluid chamber having a first plunger to, responsive to receipt of the biologic sample, mix the biologic sample with a lysis solution including adsorption beads to bind with nucleic acids of the biologic sample, wherein the trapping region includes a magnet external to the reaction-chamber circuit to secure the adsorption beads within the microfluidic reaction chamber.

5. The apparatus of claim 1, wherein the pump is disposed on a different side of the microfluidic reaction chamber relative to a side of the microfluidic reaction chamber on which a fluidic input region is disposed, the pump to move the reagent and the biologic sample from the fluidic input region and through the microfluidic reaction chamber.

6. The apparatus of claim 1, wherein the microfluidic reaction chamber includes the reaction-chamber circuit on a substrate and a lid disposed over the reaction-chamber circuit to form a via between the lid and the reaction-chamber circuit, the trapping region including a magnet external to the reaction-chamber circuit to secure paramagnetic beads bound to the nucleic acids.

* * * * *